(12) United States Patent
Grant et al.

(10) Patent No.: US 11,519,862 B2
(45) Date of Patent: Dec. 6, 2022

(54) METHODS AND SYSTEMS FOR ASSESSING QUALITY OF A MEAT PRODUCT

(71) Applicant: MEQ PROBE PTY LTD, Unley (AU)

(72) Inventors: Andrew Grant, Crafers (AU); Remo Carbone, Unley (AU); Mark Hutchinson, Unley (AU)

(73) Assignee: MEQ PROBE PTY LTD, Unley (AU)

( * ) Notice: Subject to any disclaimer, the term of this patent is extended or adjusted under 35 U.S.C. 154(b) by 466 days.

(21) Appl. No.: 16/614,082

(22) PCT Filed: May 15, 2018

(86) PCT No.: PCT/AU2018/050455
§ 371 (c)(1),
(2) Date: Nov. 15, 2019

(87) PCT Pub. No.: WO2018/209383
PCT Pub. Date: Nov. 22, 2018

(65) Prior Publication Data
US 2020/0173926 A1 Jun. 4, 2020

(30) Foreign Application Priority Data
May 16, 2017 (AU) ................................ 2017901826

(51) Int. Cl.
*G01N 21/64* (2006.01)
*G01N 33/12* (2006.01)

(52) U.S. Cl.
CPC ....... *G01N 21/6486* (2013.01); *G01N 21/645* (2013.01); *G01N 33/12* (2013.01);
(Continued)

(58) Field of Classification Search
CPC ... G01N 21/6486; G01N 21/645; G01N 33/12
See application file for complete search history.

(56) References Cited

U.S. PATENT DOCUMENTS 6,363,328 B1 * 3/2002 Nadeau .................. G01N 33/12
33/511
6,563,580 B1 * 5/2003 Aignel .................... G01N 33/12
250/910

(Continued)

FOREIGN PATENT DOCUMENTS

CN 201392319 Y 1/2010
CN 102323267 A 1/2012

(Continued)

OTHER PUBLICATIONS

Byrne et al. Non-destructive Prediction of Selected Quality Attributes of Beef by Near-infrared Reflectance Spectroscopy . . . , Meat Science, vol. 49, No. 4, 399-409, 1998 1998 Elsevier Science Ltd., (Received Sep. 10, 1997; revised version received Nov. 24, 1997; accepted Nov. 27, 1997) (Year: 1997).*

(Continued)

*Primary Examiner* — Hugh Maupin
(74) *Attorney, Agent, or Firm* — Fenwick & West LLP

(57) ABSTRACT

The present disclosure relates to methods and systems for assessing the quality of a meat product. In certain embodiments, the present disclosure provides a method of assessing quality of a meat product, the method comprising receiving data representative of light emitted from the meat product upon application of incident light to the meat product, analysing the data to determine one or more parameters indicative of quality of the meat product, and assessing the quality of the meat product on the basis of the one or more parameters.

18 Claims, 15 Drawing Sheets

(52) U.S. Cl.
CPC ............... *G01N 2021/6484* (2013.01); *G01N 2201/06113* (2013.01); *G01N 2201/08* (2013.01)

(56) References Cited

U.S. PATENT DOCUMENTS

2003/0177025 A1* 9/2003 Curkendall ............ A01K 29/00 340/573.3
2011/0128373 A1 6/2011 Goldberg

FOREIGN PATENT DOCUMENTS

| CN | 102519906 A | 6/2012 | |
|---|---|---|---|
| CN | 104458594 A | 3/2015 | |
| CN | 104914069 A | 9/2015 | |
| CN | 105209890 A | 12/2015 | |
| CN | 106501211 A | 3/2017 | |
| DE | 10 2013 008003 A1 | 11/2014 | |
| EP | 0402877 A1 | 12/1990 | |
| EP | 0444675 A2 | 9/1991 | |
| JP | H03214041 A | 9/1991 | |
| JP | 2003121351 A | 4/2003 | |
| JP | 2006030047 A | 2/2006 | |
| WO | WO-2006057990 A2 * | 6/2006 | ............ A22B 5/007 |
| WO | WO 2012/149654 A1 | 11/2012 | |

OTHER PUBLICATIONS

Khan, M. et al., "Hyperbranched Polyglycidol on Si/SiO2 Surfaces via Surface-Initiated Polymerization" Macromolecules, 2003, vol. 36, pp. 5088-5093.

Moore, E. et al., "Surface-Initiated Hyperbranched Polyglycerol as an Ultralow-Fouling Coating on Glass, Silicon, and Porous Silicon Substrates," ASC Applied Materials & Interfaces, 2014, vol. 6, No. pp. 15243-15252.

Weber, T. et al., "Bacteria-Repulsive Polyglycerol Surfaces by Grafting Polymerization onto Aminopropylated Surfaces" Langmuir, 2012, vol. 28, pp. 15916-15921.

Weber, T. et al., "Direct grafting of anti-fouling polyglycerol layers to steel and other technically relevant materials," Colloids and Surfaces B: Biointerfaces, SciVerse Science Direct, 2013, vol. 111, 7 pages.

PCT International Search Report & Written Opinion, International Application No. PCT/AU2018/050455, dated Aug. 1, 2018, 13 Pages.

European Patent Office, Extended European Search Report and Opinion, EP Patent Application No. 18802403.8, dated Feb. 11, 2021, nine pages.

Jordan, G. et al., "Non-invasive mobile monitoring of meat quality," Journal Fur Verbraucherschutz und Lebensmittelsicherheit, vol. 4, No. 1, Feb. 1, 2009, pp. 7-14.

China National Intellectual Property Administration, First Office Action, Chinese Patent Application No. 201880047240.3, dated Feb. 8, 2022, 26 pages.

Japan Patent Office, Notice of Reasons for Rejection, Japanese Patent Application No. 2020-514305, dated Feb. 28, 2022, 19 pages.

Møller, J. K. S et al. "Monitoring Chemical Changes of Dry-Cured Parma Ham During Processing by Surface Autofluorescence Spectroscopy." Journal of Agricultural and Food Chemistry, vol. 51, No. 5, Jan. 24, 2003, pp. 1224-1230.

Yu, F. et al. "Preliminary Study of Laser-Induced Fluorescence Spectroscopy Detect Chicken Meat Tenderness." The $2^{nd}$ International Conference on Information Science and Engineering, Dec. 2010, pp. 6771-6774, (with English abstract).

* cited by examiner

Prediction of Fat% using the Statistical Model (5th Oakey Cold Carcass

Prediction of Shear Force using the Linear Model (5th Oakey Cold Carcass)

Prediction of pH using Linear Model (5th Oakey Cold Carcass)

METHODS AND SYSTEMS FOR ASSESSING QUALITY OF A MEAT PRODUCT

PRIORITY CLAIM

This application claims priority to Australian Provisional Patent Application 2017901826 filed on 16 May 2017, the content of which is hereby incorporated by reference.

FIELD

The present disclosure relates to methods and systems for assessing the quality of a meat product.

BACKGROUND

An important part of the meat industry is making an assessment of the quality of meat.

Assessment of meat quality may involve assessing a variety of characteristics to ensure that meat provided to the consumer is of a desired quality. In addition, assessing the quality of meat informs a producer as to how animal characteristics, animal management and/or processing of animals influence the final quality of a meat product.

Determining meat quality often involves methods of directly assessing characteristics of the meat, such as a colour assessment, an analysis of texture and a determination of muscle pH. In some cases, this requires a sample of the meat to be tested, which imposes an additional burden and/or constraint on the processing of meat products.

In addition, processing of meat is typically undertaken on a large scale, so as to provide economic advantages associated with bulk processing. However, methods involving testing samples of meat for quality impose further burdens on bulk processing, such as introducing delays in the production process, the need for integration into the production process, and increased costs.

Accordingly, methods of assessing quality of a meat product that do not require sampling would be advantageous, and in particular methods where the product does not need to be physically interrogated.

SUMMARY

The present disclosure relates to methods and systems for assessing the quality of a meat product.

Certain embodiments of the present disclosure provide a method of assessing quality of a meat product.

Certain embodiments of the present disclosure provide a method of assessing quality of a meat product, the method comprising:

receiving data representative of light emitted from the meat product upon application of incident light to the meat product;

analysing the data to determine one or more parameters indicative of quality of the meat product; and assessing the quality of the meat product on the basis of the one or more parameters.

In certain embodiments, the meat product is a carcass, a part of a carcass, a cut of meat from the carcass, or a processed product derived from the carcass or the cut of meat.

In certain embodiments, the meat product is a red meat product.

In certain embodiments, the meat product is a product derived from a sheep, a lamb, a cow, a calf, a pig, a goat, a deer, or a horse. Other types of meat products are contemplated.

In certain embodiments, the meat product is an ovine meat product, a bovine meat product, a porcine meat product, a caprine meat product, a cervine meat product, or an equine meat product.

In certain embodiments, the meat product is a beef meat product, a veal meat product, a lamb meat product, a mutton meat product, a pig meat product, a goat meat product, a deer meat product, or a horse meat product.

The term "quality of a meat product" as used herein refers to a selected characteristic of a meat product. Examples of quality of a meat product may comprise one or more of eating quality, price point, grading, pH, fat content, tenderness, and suitability for specific purposes.

In certain embodiments, the quality of the meat product comprises eating quality.

In certain embodiments, the quality of the meat product comprises pH.

In certain embodiment, the quality of the meat product comprises a grading or scoring system. For example, the method may be used to grade or score the eating quality of the meat product.

In certain embodiments, the quality of the meat product comprises a threshold value, a minimum value, a maximum value, an assigned value, or a range of values for a quality of the meat product. The quality of the meat product may comprise one of a number of different grades, for example low, medium or high grade.

In certain embodiments, the incident light comprises light of one or more specific wavelengths. In certain embodiments, the incident light comprises one or more wavelengths over a specific range of wavelengths.

In certain embodiments, the incident light comprises non-coherent light. In certain embodiments, the incident light comprises coherent light. In certain embodiments, the incident light comprises laser light.

Methods and sources for producing incident light (coherent and/or non-coherent) of one or more wavelengths are known in the art, and commercially available.

In certain embodiments, the incident light comprises a wavelength in the range of 400 nm to 415 nm. Other wavelength ranges are contemplated.

In certain embodiments, the incident light comprises a wavelength in the range of one of 400 nm to 410 nm, 400 nm to 405 nm, 405 nm to 415 nm, 405 nm to 410 nm, or 410 nm to 415 nm, or about one of the aforementioned ranges.

In certain embodiments, the incident light comprises a wavelength in the range of one of 402 nm to 408 nm, 403 nm to 408 nm, 404 nm to 408 nm, 405 nm to 408 nm, 406 nm to 408 nm, 407 nm to 408 nm, 402 nm to 407 nm, 403 nm to 407 nm, 404 nm to 407 nm, 405 nm to 407 nm, 406 nm to 407 nm, 402 nm to 406 nm, 403 nm to 406 nm, 404 nm to 406 nm, 405 nm to 406 nm, 402 to 405 nm, 403 nm to 405 nm, 404 nm to 405 nm, 402 nm to 404 nm, 403 to 404 nm, and 402 nm to 403 nm, or about one of the aforementioned ranges.

In certain embodiments, the incident light comprises a wavelength of 405±3 nm.

In certain embodiments, the incident light comprises a wavelength of about 404 nm or about 405 nm.

The term "about" or "approximately" means an acceptable error for a particular value, which depends in part on how the value is measured or determined. In certain embodiments, "about" can mean 1 or more standard deviations. When the antecedent term "about" is applied to a recited range or value it denotes an approximation within the deviation in the range or value known or expected in the art from the measurements method.

In certain embodiments, the incident light is transmitted to the meat product via an optical fibre. In certain embodiments, the incident light is transmitted to a probe via an optical fibre.

In certain embodiments, the incident light is applied to the meat product via a probe. In certain embodiments, the incident light is applied to the meat product via a probe below the surface of the meat product.

In certain embodiments, the incident light is applied to the meat product via an optical fibre. In certain embodiments, the incident light is applied to the meat product via an optical fibre probe. In certain embodiments, the incident light is applied to the meat product via an optical fibre in a needle.

In certain embodiments, the incident light is applied to the surface of the meat product. In certain embodiments, the incident light is applied to below the surface of the meat product.

In certain embodiments, the light emitted from the meat product comprises light with a wavelength in the range from 440 to 800 nm. Other wavelengths are contemplated.

In certain embodiments, the method comprises detecting light emitted from the meat product. Methods for detecting light are known in the art. In certain embodiments, the light emitted from the meat product comprises light with a wavelength in the range selected from one of 400 nm to 800 nm, 450 to 800 nm, 500 to 800 nm, 550 nm to 800 nm, 600 nm to 800 nm, 650 nm to 800 nm, 700 to 800 nm, 750 to 800 nm, 400 nm to 750 nm, 450 to 750 nm, 500 to 750 nm, 550 nm to 750 nm, 600 nm to 750 nm, 650 nm to 750 nm, 700 to 750 nm, 400 nm to 700 nm, 450 to 700 nm, 500 to 700 nm, 550 nm to 700 nm, 600 nm to 700 nm, 650 nm to 700 nm, 400 nm to 650 nm, 450 to 650 nm, 500 to 650 nm, 550 nm to 650 nm, 600 nm to 650 nm, 400 nm to 600 nm, 450 to 600 nm, 500 to 600 nm, 550 nm to 600 nm, 400 nm to 550 nm, 450 nm to 550 nm, 500 to 550 nm, 400 nm to 500 nm, 450 to 500 nm, or 400 nm to 450 nm, or about one of the aforementioned ranges.

In certain embodiments, the light emitted from the meat product comprises reflected light.

In certain embodiments, the light emitted from the meat product comprises autofluorescent excited light.

In certain embodiments, the incident light induces autofluorescence in the meat product. In certain embodiments, the emitted light comprises autofluorescent light excited in the meat product by application of the incident light to the meat product.

In certain embodiments, the autofluoresence is excited by the application of laser light to the meat product.

In certain embodiments, the method comprises detecting emitted light from the meat product upon application of the incident light to the meat product. Methods for detecting light and converting it into data are known in the art.

In certain embodiments, the received data from the meat product comprises data associated with one or more wavelengths of light.

In certain embodiments, the received data from the meat product comprises data associated with one or more wavelengths of light in the range from 440 to 800 nm.

In certain embodiments, the received data from the meat product comprises data associated with one or more wavelengths of light in the range selected from one of 400 nm to 800 nm, 450 to 800 nm, 500 to 800 nm, 550 nm to 800 nm, 600 nm to 800 nm, 650 nm to 800 nm, 700 to 800 nm, 750 to 800 nm, 400 nm to 750 nm, 450 to 750 nm, 500 to 750 nm, 550 nm to 750 nm, 600 nm to 750 nm, 650 nm to 750 nm, 700 nm to 750 nm, 400 nm to 700 nm, 450 to 700 nm, 500 to 700 nm, 550 nm to 700 nm, 600 nm to 700 nm, 650 nm to 700 nm, 400 nm to 650 nm, 450 to 650 nm, 500 to 650 nm, 550 nm to 650 nm, 600 nm to 650 nm, 400 nm to 600 nm, 450 to 600 nm, 500 to 600 nm, 550 nm to 600 nm, 400 nm to 550 nm, 450 to 550 nm, 500 to 550 nm, 400 nm to 500 nm, 450 to 500 nm, or 400 nm to 450 nm, or about one of the aforementioned ranges, or about one of the aforementioned ranges.

In certain embodiments, the received data from the meat product comprises data associated with a spectrum of light. In certain embodiments, the received data from the meat product comprises data associated with autofluorescence excited light. In certain embodiments, the received data from the meat product comprises data associated with spectral autofluorescent light.

In certain embodiments, the received data from the meat product comprises data associated with light with a wavelength in the range from 440 to 800 nm.

In certain embodiments, the received data comprises spectral data emitted from the meat product. In certain embodiments, the received data comprises spectral data representative of autofluoresence excited in the meat product.

In certain embodiments, the spectral data comprises data associated with light in the range of 440 nm to 800 nm.

In certain embodiments, the spectral data comprises data associated with light with a wavelength in the range selected from one of 400 nm to 800 nm, 450 to 800 nm, 500 to 800 nm, 550 nm to 800 nm, 600 nm to 800 nm, 650 nm to 800 nm, 700 to 800 nm, 750 to 800 nm, 400 nm to 750 nm, 450 to 750 nm, 500 to 750 nm, 550 nm to 750 nm, 600 nm to 750 nm, 650 nm to 750 nm, 700 to 750 nm, 400 nm to 700 nm, 450 to 700 nm, 500 to 700 nm, 550 nm to 700 nm, 600 nm to 700 nm, 650 nm to 700 nm, 400 nm to 650 nm, 450 to 650 nm, 500 to 650 nm, 550 nm to 650 nm, 600 nm to 650 nm, 400 nm to 600 nm, 450 to 600 nm, 500 to 600 nm, 550 nm to 600 nm, 400 nm to 550 nm, 450 to 550 nm, 500 to 550 nm, 400 nm to 500 nm, 450 to 500 nm, or 400 nm to 450 nm, or about one of the aforementioned ranges.

In certain embodiments, the one or more parameters indicative of quality of the meat comprises a single parameter. In certain embodiments, the one or more parameters indicative of quality of meat comprise two parameters. In certain embodiments, the one or more parameters indicative of quality of meat comprise a plurality of parameters.

Examples of parameters include a parameter indicative of carcass weight (or part of a carcass), a parameter indicative of fat content in the meat product, a parameter indicative of fat mass in the meat product, a parameter indicative of a measurement (size, area, and/or depth) of a specific muscle or region in a carcass, a parameter indicative of acidity and/or alkalinity (such as pH) in the meat product, one or more colours of the meat product, shear force (SF), intramuscular fat (IMF), species of animal, time of year, or a combination of any one or more of the aforementioned parameters.

In certain embodiments, the one or more parameters comprises one or more of the following:
 a parameter indicative of carcass weight;
 a parameter indicative of carcass temperature;
 a measure of tissue depth;
 a parameter indicative of intra-muscular fat (IMF parameter); a parameter indicative of shear force (SF parameter);
 species of animal; and
 time of year.

In certain embodiments, the one or more parameters comprises one or more of the following:

a parameter indicative of hot carcass weight (HCWT parameter); (at least for a sheep or a lamb) a measure of tissue depth over a 12th rib (GRfat parameter);

a parameter indicative of an amount of fat over an eye muscle (FatC parameter);

a parameter indicative of intra-muscular fat (IMF parameter); and a parameter indicative of shear force (SF parameter).

In certain embodiments, the one or more parameters comprise a parameter indicative of the temperature of the meat product.

In certain embodiments, the one or more parameters comprise a parameter indicative of intra-muscular fat (IMF parameter) and a parameter indicative of shear force (SF parameter).

In certain embodiments, the data is analysed using one or more models to predict the one or more parameters.

In certain embodiments, the one or more models comprise linear statistical models. In certain embodiments, the one or more models comprise non-linear models.

In certain embodiments, the one or more models are created using a data minimisation approach. In certain embodiments, the data minimisation approach includes employing Akaike's Information Criterion. Other methods for data minimisation are contemplated.

In certain embodiments, the one or more models comprise non-linear models.

In certain embodiments, the one or more models comprise logistic regression.

In certain embodiments, the one or more models are created using training data including data representative of light emitted from a plurality of sample meat products upon application of incident light to the sample meat products, each sample meat product having pre-determined values for the one or more parameters.

In certain embodiments, the one or more models are created using machine learning.

In certain embodiments, the one or more models are created using neural networks.

In certain embodiments, the one or models are created using deep learning.

In certain embodiments, the data comprises spectral data which is processed prior to analysis to reduce a number of data points across the spectral range.

In certain embodiments, the quality of the meat product comprises eating quality.

In certain embodiments, the quality of the meat product comprises pH.

In certain embodiments, the method is used to grade, score or classify a meat product for quality.

Certain embodiments of the present disclosure provide a meat product graded, scored or classified according to a method as described herein.

Certain embodiments of the present disclosure provide software comprising a series of instructions executable by a processor to carry out a method as described herein.

Certain embodiments of the present disclosure provide software for use with a computer comprising a processor and memory for storing the software, the software comprising a series of instructions executable by the processor to carry out a method as described herein.

Certain embodiments of the present disclosure provide a system for assessing quality of a meat product.

Certain embodiments of the present disclosure provide a system for assessing quality of a meat product, the system comprising:

a light source for applying incident light to the meat product;

a measuring device for producing data representative of light emitted from the meat product upon application of incident light to the meat product;

a processor;

a memory; and software resident in the memory accessible to the processor, the software comprising a series of instructions executable by the processor to carry out a method as described herein.

Certain embodiments of the present disclosure provide a system for assessing quality of a meat product, the system comprising:

a light source for applying incident light to the meat product;

a measuring device for producing data representative of light emitted from the meat product upon application of incident light to the meat product;

a processor;

a memory; and software resident in the memory accessible to the processor, the software comprising a series of instructions executable by the processor to analyse the data to determine one or more parameters indicative of quality of the meat product, and provide a measure of the quality of the meat product on the basis of the one or more parameters.

Meat products, and the quality of meat products, are as described herein.

Sources of light for producing incident light are known in the art. Details of incident light are as described herein.

In certain embodiments, the source of incident light produces light comprising a wavelength in the range of one of 400 nm to 415 nm. Other wavelength ranges are contemplated.

In certain embodiments, the source of incident light produces light comprising a wavelength in the range of one of 400 nm to 410 nm, 400 nm to 405 nm, 405 nm to 415 nm, 405 nm to 410 nm, or 410 nm to 415 nm, or about one of the aforementioned ranges.

In certain embodiments, the source of incident light produces light comprising a wavelength in the range of 402 nm to 408 nm, 403 nm to 408 nm, 404 nm to 408 nm, 405 nm to 408 nm, 406 nm to 408 nm, 407 nm to 408 nm, 402 nm to 407 nm, 403 nm to 407 nm, 404 nm to 407 nm, 405 nm to 407 nm, 406 nm to 407 nm, 402 nm to 406 nm, 403 nm to 406 nm, 404 nm to 406 nm, 405 nm to 406 nm, 402 to 405 nm, 403 nm to 405 nm, 404 nm to 405 nm, 402 nm to 404 nm, 403 to 404 nm, and 402 nm to 403 nm, or about one of the aforementioned ranges.

In certain embodiments, the source of incident light produces light comprising a wavelength of 405±3 nm.

In certain embodiments, the source of incident light produces light comprising a wavelength of about 404 nm or about 405 nm.

In certain embodiments, the measuring device detects and measures the emitted light.

Details of light emitted from a meat product are as described herein.

In certain embodiments, the measuring device measures light comprising a wavelength in the range selected from one of 400 nm to 800 nm, 450 to 800 nm, 500 to 800 nm, 550 nm to 800 nm, 600 nm to 800 nm, 650 nm to 800 nm, 700 to 800 nm, 750 to 800 nm, 400 nm to 750 nm, 450 to 750 nm, 500 to 750 nm, 550 nm to 750 nm, 600 nm to 750 nm, 650 nm to 750 nm, 700 to 750 nm, 400 nm to 700 nm, 450 to 700 nm, 500 to 700 nm, 550 nm to 700 nm, 600 nm to 700 nm, 650 nm to 700 nm, 400 nm to 650 nm, 450 to 650 nm, 500 to 650 nm, 550 nm to 650 nm, 600 nm to 650 nm, 400 nm to 600 nm, 450 to 600 nm, 500 to 600 nm, 550 nm to 600 nm, 400 nm to 550 nm, 450 to 550 nm, 500 to 550 nm, 400 nm to 500 nm, 450 to 500 nm, or 400 nm to 450 nm, or about one of the aforementioned ranges.

In certain embodiments, the measuring device measures light comprising a wavelength in the range from 440 to 800 nm.

In certain embodiments, the light source and/or the measuring device comprise part of a probe. Other arrangements are contemplated.

In certain embodiments, the light emitted from the meat product comprises light with a wavelength in the range from 440 to 800 nm.

In certain embodiments, the light emitted from the meat product comprises light with a wavelength in the range from 400 nm to 800 nm, 450 to 800 nm, 500 to 800 nm, 550 nm to 800 nm, 600 nm to 800 nm, 650 nm to 800 nm, 700 to 800 nm, 750 to 800 nm, 400 nm to 750 nm, 450 to 750 nm, 500 to 750 nm, 550 nm to 750 nm, 600 nm to 750 nm, 650 nm to 750 nm, 700 to 750 nm, 400 nm to 700 nm, 450 to 700 nm, 500 to 700 nm, 550 nm to 700 nm, 600 nm to 700 nm, 650 nm to 700 nm, 400 nm to 650 nm, 450 to 650 nm, 500 to 650 nm, 550 nm to 650 nm, 600 nm to 650 nm, 400 nm to 600 nm, 450 to 600 nm, 500 to 600 nm, 550 nm to 600 nm, 400 nm to 550 nm, 450 to 550 nm, 500 to 550 nm, 400 nm to 500 nm, 450 to 500 nm, or 400 nm to 450 nm, or about one of the aforementioned ranges.

Methods and devices for measuring light and converting the light measured into data are known in the art.

In certain embodiments, the measuring device comprises a spectrometer.

Processors, memory and software are as described herein.

In certain embodiments, the processor, the memory and the software are located so as to be in data connection with the probe.

Processing of data is as described herein.

In certain embodiments, the light source and the measuring device comprise part of a probe, and the processor, the memory and the software are located remotely from the probe and receive the data over the internet.

One or more parameters indicative of quality, and methods for their determination, are as described herein. The use of the one or more parameters to provide a measure of the quality of a meat product is as described herein.

In certain embodiments, the quality of the meat product comprises eating quality.

In certain embodiments, the quality of the meat product comprises pH.

In certain embodiments, the quality of meat product comprises fat content (such as intramuscular fat content) and/or tenderness (such as shear force).

In certain embodiments, the system is used to grade, score or classify a meat product for quality.

Certain embodiments of the present disclosure provide a meat product graded, scored or classified using a system as described herein.

Certain embodiments of the present disclosure provide a method of creating one or more models for assessing quality of a meat product.

Certain embodiments of the present disclosure provide a method of creating one or more models for assessing quality of a meat product, the method comprising:

for a plurality of sample meat products, receiving data representative of light emitted from the sample meat product upon application of incident light to the sample meat product;
for the sample meat products, receiving one or more pre-determined values;
using the data and one or more pre-determined values to create one or more models to predict one or more parameters indicative of quality of the meat product.

Meat products, and the quality of meat products, are as described herein.

Details of incident light are as described herein.

In certain embodiments, the incident light comprises light with a wavelength in the range of one of 400 nm to 415 nm. Other wavelength ranges are contemplated.

In certain embodiments, the incident light comprises light with a wavelength in the range of one of 400 nm to 410 nm, 400 nm to 405 nm, 405 nm to 415 nm, 405 nm to 410 nm, or 410 nm to 415 nm, or about one of the aforementioned ranges.

In certain embodiments, the incident light comprises light with a wavelength in the range of 402 nm to 408 nm, 403 nm to 408 nm, 404 nm to 408 nm, 405 nm to 408 nm, 406 nm to 408 nm, 407 nm to 408 nm, 402 nm to 407 nm, 403 nm to 407 nm, 404 nm to 407 nm, 405 nm to 407 nm, 406 nm to 407 nm, 402 nm to 406 nm, 403 nm to 406 nm, 404 nm to 406 nm, 405 nm to 406 nm, 402 to 405 nm, 403 nm to 405 nm, 404 nm to 405 nm, 402 nm to 404 nm, 403 to 404 nm, and 402 nm to 403 nm, or about one of the aforementioned ranges.

In certain embodiments, the incident light comprises light with wavelength of 405±3 nm.

In certain embodiments, the light comprises light with a wavelength of about 404 nm or about 405 nm.

In certain embodiments, the light emitted from the sample comprises light with a wavelength in the range from 440 to 800 nm.

In certain embodiments, the light emitted from the sample comprises light with a wavelength in the range selected from 400 nm to 800 nm, 450 to 800 nm, 500 to 800 nm, 550 nm to 800 nm, 600 nm to 800 nm, 650 nm to 800 nm, 700 to 800 nm, 750 to 800 nm, 400 nm to 750 nm, 450 to 750 nm, 500 to 750 nm, 550 nm to 750 nm, 600 nm to 750 nm, 650 nm to 750 nm, 700 to 750 nm, 400 nm to 700 nm, 450 to 700 nm, 500 to 700 nm, 550 nm to 700 nm, 600 nm to 700 nm, 650 nm to 700 nm, 400 nm to 650 nm, 450 to 650 nm, 500 to 650 nm, 550 nm to 650 nm, 600 nm to 650 nm, 400 nm to 600 nm, 450 to 600 nm, 500 to 600 nm, 550 nm to 600 nm, 400 nm to 550 nm, 450 to 550 nm, 500 to 550 nm, 400 nm to 500 nm, 450 to 500 nm, or 400 nm to 450 nm, or about one of the aforementioned ranges.

Details of light emitted from a meat product are as described herein.

Methods and devices for measuring light and converting the light measured into data are as described herein.

In certain embodiments, the pre-determined values comprise a parameter indicative of carcass weight (or part of a carcass), a parameter indicative of fat content in the meat product, a parameter indicative of fat mass in the meat product, a parameter indicative of a measurement (size, area, an/or depth) of a specific muscle in a carcass, a parameter indicative of acidity and/or alkalinity (such as pH) in the meat product, one or more colours of the meat product, shear force (SF), intramuscular fat (IMF), or a combination of any one or more of the aforementioned parameters.

In certain embodiments, the pre-determined values comprise one or more parameters as follows:

a parameter indicative of carcass weight;
a parameter indicative of carcass temperature;
a measure of tissue depth;
a parameter indicative of intra-muscular fat (IMF parameter); and
a parameter indicative of shear force (SF parameter).

In certain embodiments, the predetermined values comprise one or more parameters as follows:
a parameter indicative of hot carcass weight (HCWT parameter);
(at least for a sheep or lamb) a measure of tissue depth over a 12th rib (GRfat parameter);
a parameter indicative of an amount of fat over an eye muscle (FatC parameter);
a parameter indicative of intra-muscular fat (IMF parameter); and
a parameter indicative of shear force (SF parameter).

In certain embodiments, the data comprises spectral data which is processed prior to using the spectral data to create one or more models.

In certain embodiments, the one or more models comprise linear statistical models. In certain embodiments, the one or more models comprise non-linear statistical models.

In certain embodiments, the one or more models comprise logistic regression.

In certain embodiments, the one or more models are created using machine learning.

In certain embodiments, the one or more models are created using neural networks.

In certain embodiments, the one or models are created using deep learning.

In certain embodiments, the one or more models are created using a data minimisation approach. In certain embodiments, the data minimisation approach comprises employing Akaike's Information Criterion.

In certain embodiments, the one or more models are created using training data including data representative of light emitted from a plurality of sample meat products upon application of incident light to the sample meat products, each sample meat product having pre-determined values for the one or more parameters.

In certain embodiments, a model as created by a method described herein is used in a system to grade, score or classify a meat product for quality.

BRIEF DESCRIPTION OF DRAWINGS

Embodiments of the present disclosure will now be described, by way of example only, with reference to the accompanying drawings, in which.

DETAILED DESCRIPTION

Figure 1:
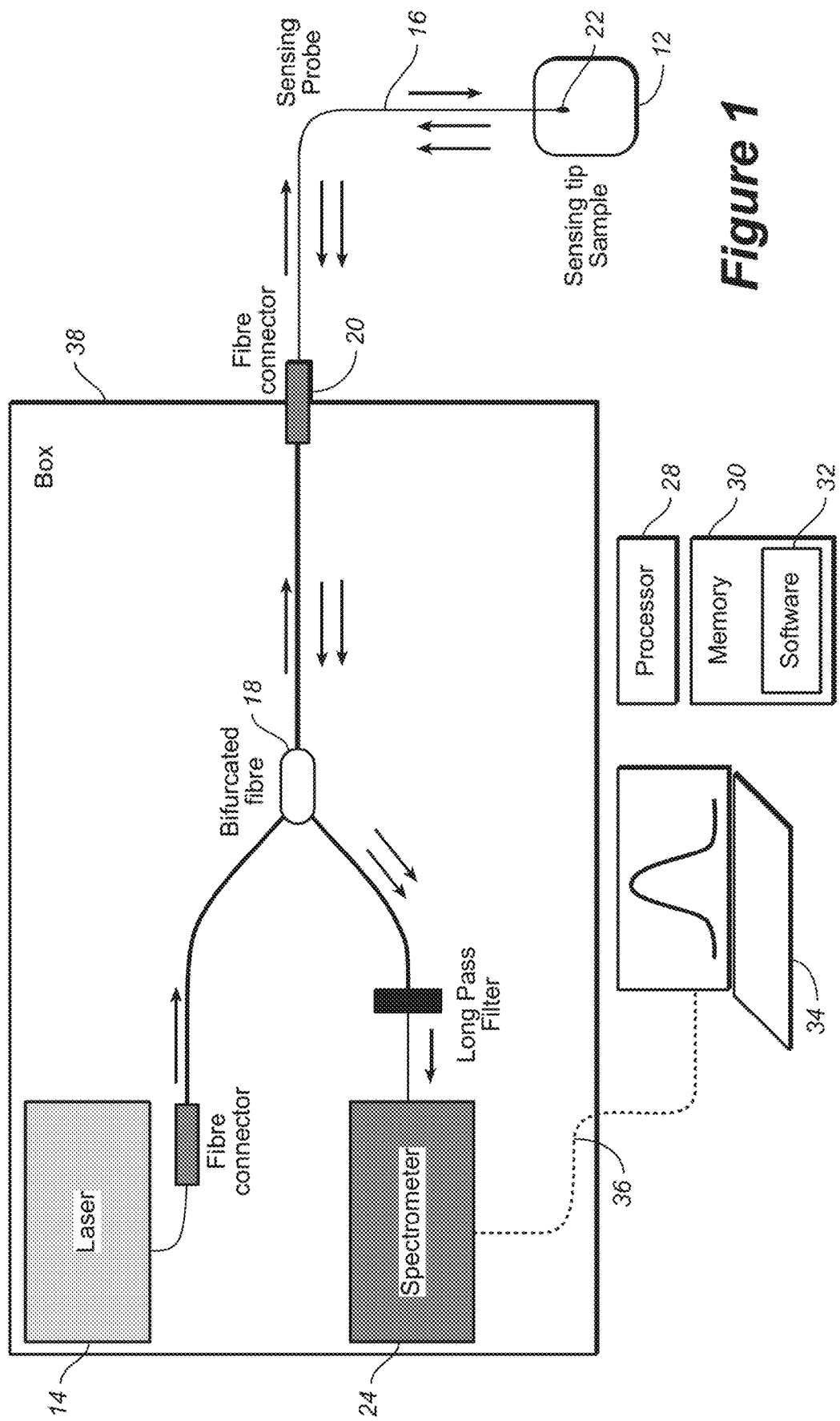
FIG. 1 is a representation of a system for assessing quality of a meat product according to one embodiment.

An embodiment of a system 10 for assessing quality of a meat product 12 is shown in FIG. 1.

The system 10 includes a light source, which in this embodiment is a blue laser 14 having a wavelength of about 404 nm. The laser 14 is connected to a fibre probe 16 through a bifurcated optical fibre 18 and fibre connector 20. The fibre probe 16 is shown inserted into the meat product 12 in order to apply incident light from the laser 14 to the meat product 12. Typically, the probe is inserted to a depth of 2 to 6 cm, but other depths are applicable, and the present disclosure contemplates the use of the probe externally to the meat product.

The meat product 12 may be a whole carcass, a side of meat or any cut of meat, for example meat suitable for wholesale or retail sale. The present disclosure may be used to assess the quality of a red meat product, for example lamb, beef, pork, venison, goat, or horse.

In an embodiment, the fibre probe 16 is inserted around the rib eye (the outer side of the rib) of a carcass. Penetration depths of approximately 20-40 mm for lamb and 40-60 mm for beef have been successfully trialled. Multi-probing of the carcass to assess multiple muscle groups may also be performed.

The application of incident light from the laser 14 to the meat product 12 causes the meat product 12 to autofluoresce and emit light. The fibre probe 16 has a sensing tip 22, which receives the light emitted from the meat product 12. This emitted light passes through the bifurcated fibre 18 to a measuring device, which in this embodiment is a spectrometer 24. A long pass filter 26 is used to suppress laser light background.

The spectrometer 24 converts the emitted light into spectral data representative of the autofluorescence excited in the meat product 12. The spectral data may comprise a measurement of intensity of the emitted light across a range of wavelengths, for example 440 nm to 800 nm. Such measurements may be taken at different intervals across the range of wavelengths and multiple measurements may be taken for each interval.

The system 10 further includes a processor 28, a memory 30 and software 32 resident in the memory 30 and accessible to the processor 28. In this embodiment, the processor 28 and memory 30 are part of a computer 34, which is in data communication 36 with the spectrometer 24.

The computer 34 may be co-located with the other components of the system 10 (hereafter referred to as the optical apparatus 38), or may be located remotely and in data communication with the spectrometer 24 over a data network, such as a LAN or the Internet. It may be physically connected to the spectrometer by a cable or in wireless communication. Alternatively, data from the spectrometer 24 may be saved, for example, on a memory card and later transferred to the computer 34 for analysis and/or stored on the cloud. It will be appreciated that the disclosure covers all means of transferring data from the spectrometer 24 to the computer 34, and all different forms the computer 34 may take including a desktop computer, laptop or mobile device.

The optical apparatus 38, with or without the computer 34 may be portable. This may enable a user to walk alongside a continuously moving abattoir chain carrying meat products and probe the meat products, or to probe meat products in a chiller without removing them from the chiller. For example, components of the optical apparatus 38 and control hardware 34 may be mounted into a pelican style case and attached to a harness. This allows the complete setup to be worn, for example as a backpack, while the measurements are being taken. A continuous connection to mains power is not required.

Figure 2:
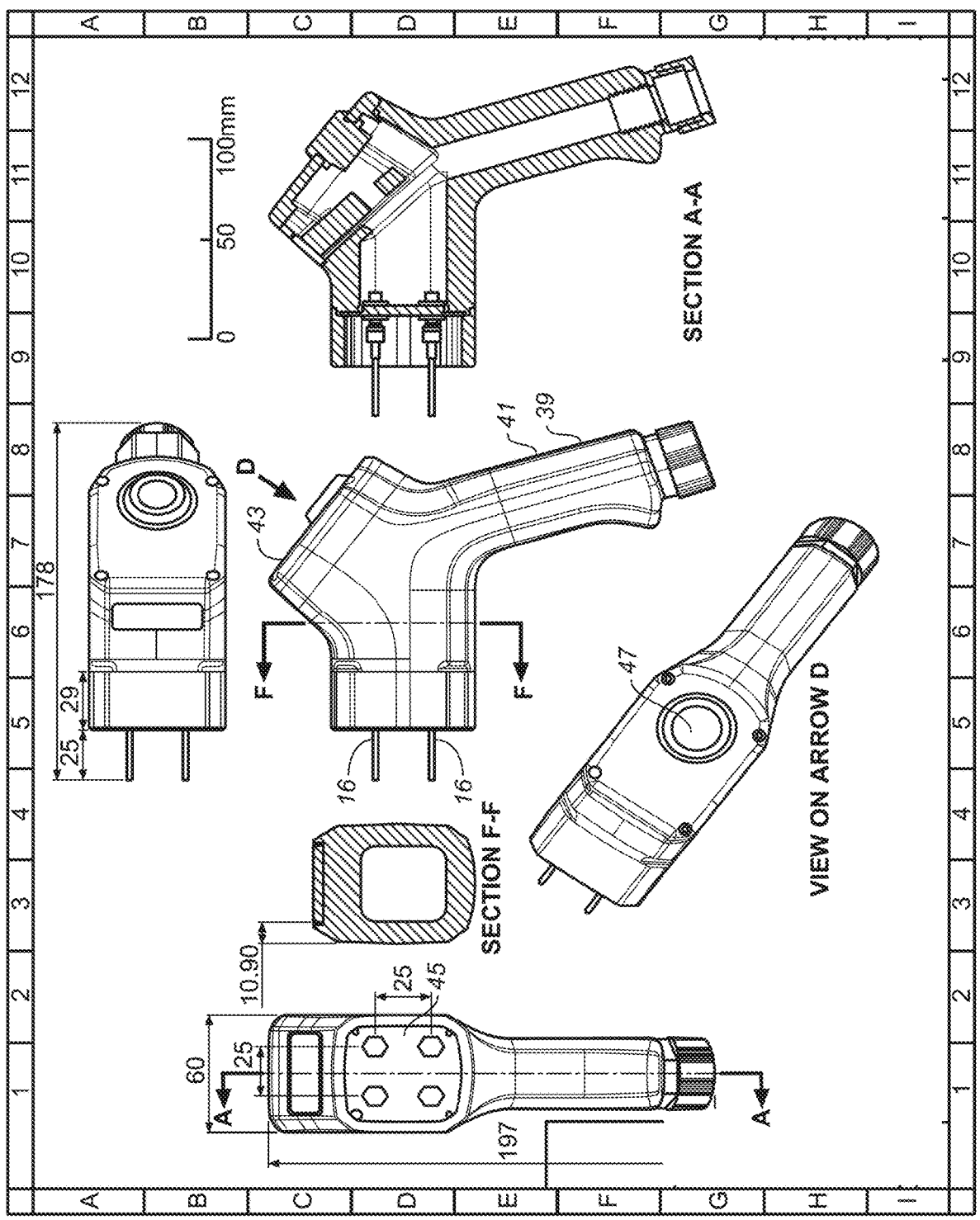
FIG. 2 includes side, top, sectional and front views of a housing for a probe according to one embodiment.

The optical fibre probe 16 may be housed in a gun shaped housing 39 as shown in FIG. 2. The housing body 41 and top cover 43 in this embodiment is made from CNC machined ABS plastic. The front plate 45 and probes 16 are made from Stainless Steel. The probes 16 are 3 mm outer diameter×1 mm inner diameter×75 mm length tubes with a taper and a M3 thread. A clear polycarbonate window 47 is included in the top cover 43, sealed with a food grade silicone. The housing 39 may facilitate ease of inserting and operating the probes 16. For example, the length of the probes 16 extending beyond the housing 39 may be set to a desired depth of insertion for the meat product being analysed. It will be appreciated that other shapes and materials of housing 39 may alternatively be used.

Other hardware or equipment may be used in conjunction with the system 10, for example, a barcode scanner for reading barcodes identifying the meat products 12, so that a particular product 12 and its measured spectral data can be associated.

Different embodiments of the optical apparatus 38 have been trialled. In a first version, the optical apparatus 38 included a 405 nm continuous-wave (CW) laser 14 delivering 15 mw of power, a UV/Vis Flame spectrometer 24 (integration time 100 ms-200 ms) collecting all wavelengths from 350 nm-1100 nm, a 407 nm long pass filter 26, a 200 uM multimodal bifurcated fibre 18 to combine the laser 12 and spectrometer 24, a 200 uM multimodal fibre for combined delivery and collection of the signal and a stainless steel needle 16 for delivery of the fibre into the meat product 12.

In a second version, the optical apparatus 38 was designed for taking multiple measurements at once. The optical apparatus 38 included the components of the first version except that four 200 uM multimobal fibres for combined delivery and collection of signal were used, and also a PS Jena 1×6 optical splitter for multiple samples. The components were all mounted in a pelican style case for portability.

In a third version, also designed for taking multiple measurements at once, the optical apparatus 38 included a 405 nm CW laser 14 for each needle 16, the lasers 14 delivering 10-40 mw of power, a UV/Vis Flame spectrometer 24 collecting all wavelengths from 350 nm-1100 nm, a 200 um bifurcated bundle 18 (4×fibres) delivering light to the spectrometer 24 and a 420 nm filter set 26, all mounted in a pelican style case for portability.

Different versions of the control hardware 34 were also trialled to control turning the laser/s 14 on/off, collect data from the spectrometer 24 and control a barcode scanner. The code was custom made and controlled using a beaglebone. One version of the control hardware 34 includes a 4S LiPo Battery 14.7V, a beaglebone for software control of components, an additional custom board for control of lasers (inputs controlled by the beaglebone), voltage regulated to ~5-6V and integrated with a wireless barcode scanner. In operation, spectral data measurements are taken using the optical apparatus 38 of FIG. 1. As meat is moved along a meat processing line, the probe 16 may be inserted into the meat at a depth of 20-60 mm, the laser 14 activated and resulting autofluoresence in the meat measured by the spectrometer 24. A barcode associated with the meat may be scanned to obtain an identification number and the spectral data generated by the spectrometer 24 may be labelled using the identification number.

Trials were performed probing hot carcasses (less than 30 minutes since kill) and cold carcasses (12-24 hours in a 4° C. chiller). The hot and cold scanning took around 3 hours, and a transition time of around 15-30 minutes was used when transitioning the probe from hot to cold and vice versa. It is expected that end use will likely be 6-10 hours and the probe will likely remain in the hot or cold environment for at least 3 hours. It is expected that a scanning run will be unlikely to experience frequent thermal cycles (in/out of the chiller in less than 30 minutes).

The meat was probed as it travelled on a continuously moving abattoir chain at a speed of approximately 8-12 carcasses per minute. The environmental temperature during hot scanning was approximately 15-35° C. and the environmental temperature during cold scanning was approximately 1-15° C. The scanning of cold meat products was done either as carcasses exited the chiller on an abattoir chain or while the carcasses were stationary in the chiller. Four scans were taken on the hot carcass and four scans taken 24 hours post mortem on the cold carcass. A 200 g meat sample was taken, labelled and aged at 4° C. The meat sample was assessed for defined variables including IMF, shear force, pH and colour. Details of some of the variables are given in the table below.

| Test | Measure | Trait | Relevance |
| --- | --- | --- | --- |
| Shear Force | newton force required to slice meat | tenderness | mid/high |

-continued

| Test | Measure | Trait | Relevance |
|---|---|---|---|
| IMF | chemical lean and fat percentage | marbling and juiciness | high |
| pH | ultimate pH of carcasses | many eq factors | high |
| Temperature | in abattoir temp probe | effect chiller management and slightly eq | mid |
| Melting point (when fat starts to dissolve) | When fat starts to dissolve: | the lower the melting put the higher the eating quality | |
| Temperature | in abattoir temp probe | effect chiller management and slightly eq | mid |

The spectral data and identification number may then be sent to a computer in which the software 32 is installed (for example, at a remote location).

The spectral data may then be processed utilising one or more of the following steps:

Data clearing may be performed to remove saturated spectra. Spectral data below 440/450 nm or above 800 nm may be cut off.

Out of range spectra may be removed.

Multiple spectra may be averaged to get one spectrum per sample.

Spectra may be normalised to a local maxima.

Data points may be averaged to reduce the number of response variables in a set (for example the resolution of the spectral data may be reduced by 10×).

Figure 3:
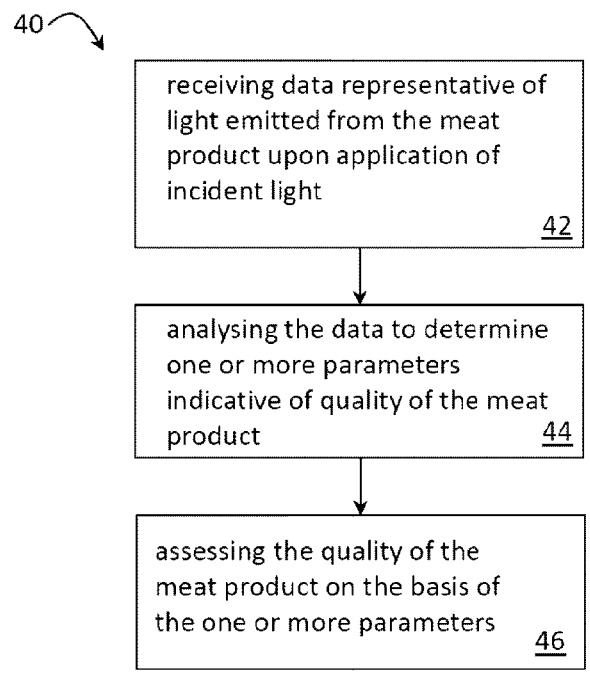
FIG. 3 is a flow chart representative of a method of assessing quality of a meat product according to one embodiment.

The software 32 includes a series of instructions executable by the processor 28 to carry out a method to analyse the data to determine one or more parameters indicative of quality of the meat product 12. With reference to FIG. 3, the method 40 includes the steps of receiving 42 data representative of light emitted from the meat product 12 upon application of incident light to the meat product 12; analysing 44 the data to determine one or more parameters indicative of quality of the meat product 12; and assessing 46 the quality of the meat product 12 on the basis of the one or more parameters.

The analysis 44 of data may involve using one or more models to predict the one or more parameters from the data output from the spectrometer 24. Based on these predictions, the quality of the meat product 12 can be assessed 46.

The one or more parameters may be predicted values of properties of the meat product, or a range of likely values for these properties (for example, a value+/−an error). Alternatively, the one or more parameters may be a categorisation of a property of the meat product into one of a plurality of categories relating to a property of the meat product, or as being above or below a threshold.

Figure 4:
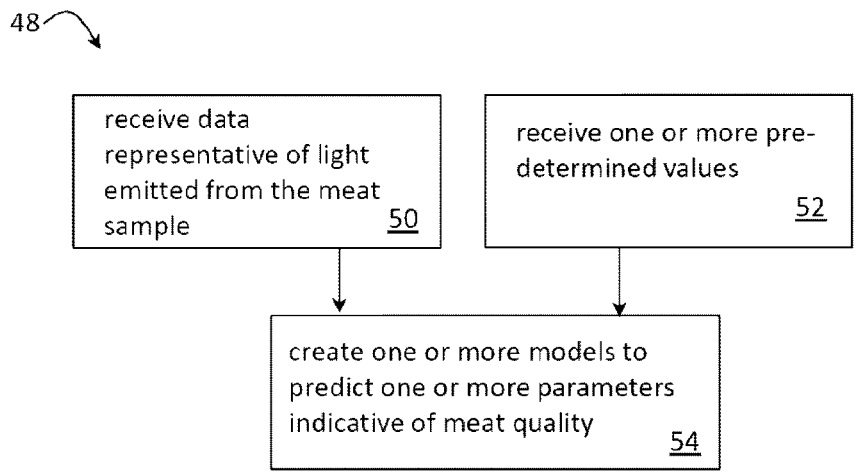
FIG. 4 is a flow chart representative of a method of creating one or more models for assessing quality of a meat product according to one embodiment.

FIG. 4 depicts a method 48 of creating one or more models for assessing quality of a meat product. The method 48 may be implemented in software and comprises, for a plurality of sample meat products, receiving data 50 representative of light emitted from the sample meat product upon application of incident light to the sample meat product; for the sample meat products, receiving one or more pre-determined values 52; and using the data and one or more pre-determined values to create one or more models 54 to predict one or more parameters indicative of quality of the meat product. The models may be created using linear statistical methods or supervised machine learning algorithms. Other models are contemplated. A prediction model may thus be created for each variable by spectral signals/signatures/fingerprints. Neural network and deep learning approaches may be applied to the data 50 to increase predictability beyond what the linear models can achieve.

Using the system and software described, it was found that parameters of lamb meat and beef meat, utilised as meat products indicative of other red meats, could be predicted at line speed (in hot, cold and chilled samples) with sufficient accuracy to assess the quality of the meat product.

Persons skilled in the art will appreciate that the software 32 could be supplied in a number of ways; for example on a computer readable medium, such as a disc or a memory of the computer 34, or as a data signal, such as by transmission from a server.

It will also be appreciated that variations on the above system and method are possible. For example, the probe 16 may be inserted into the meat product in multiple positions, with measurements taken in each position and/or multiple measurements taken with the probe 16 in the same position. In another embodiment, multiple probes may be used to take a number of simultaneous measurements of autofluoresence.

Examples of the development of the system and method are given below. It is to be understood that the following description is for the purpose of describing particular embodiments only and is not intended to be limiting with respect to the above description.

EXAMPLE 1

Measurement and Sampling Carcasses for Meat Eating Quality Analysis

The following measurements were obtained for 200 lamb carcasses:

HCWT—hot carcass weight;
GRfat—a measure of tissue depth over the 12th rib (mainly fat);
EMW—eye muscle width;
EMD—eye muscle depth;
FatC—the amount of fat over the eye muscle;
EMA—eye muscle area;
pHu_loin—the pH of the eye muscle;
pHu_temp—the temperature of the eye muscle at the time of measuring the pHu;
L—measure of colour lightness;
a—measure of colour redness;
b—measure of colour yellowness;
SF—shear force; and
IMF—intra-muscular fat.

These measurements are given in Appendix A (Table 3) below.

Methodology

The measurements were obtained as follows:

(i) Carcass Measurement

Hot carcase weight (HCWT), depth of tissue at the GR site (GR depth), cfat thickness, and eye muscle area (EMA) at the 12th rib were measured. HCWT was provided by the processing plant. GR depth (mm) was measured with a GR knife 4-6 h post-mortem at the $12^{th}$ rib, 110 mm from the spinal column on the right-hand side of the carcass.

Following overnight chilling, at approximately 21 h post-mortem, 13-15 cm of the left section of the loin (m. longissimus thoracic et lumborum; LL) was removed from above the $12^{th}$ rib. From this section of LL, fresh eye muscle colour was measured after the exposed section of LL was allowed to 'bloom' for 30-60 minutes. A Minolta Chromameter was used to measure lightness (L*), redness (a*) and yellowness (b*) of the loin. pH levels were recorded as an estimate of ultimate pH (pHu loin) using TPS WP-80 pH meter linked to temperature sensor and an Ionode pH probe. Eye muscle width (EMW; mm), eye muscle depth (EMD; mm) and cFat (mm) were measured with digital calipers on the exposed surface of the LL. EMA was calculated from EMW and EMD according to the equation: EMA=EMW*EMD*0.008.

(ii) Sample Collection and Processing

At approximately 24 h post-mortem, the fat and epimysium were removed from the section of the LL that was previously removed from the carcass. Samples for shear force (SF5; 65 g) and intramuscular fat (IMF; 40 g) were collected. IMF samples were frozen immediately after collection.

The SF5 samples were vacuum packed and aged at 4-5° C. for five days prior to freezing at−20° C.

(iii) Shear Force Measurement

Frozen 65 g LL samples were placed into a water bath at 71° C. for 35 min to cook, and then immersed in chilled water prior to processing. The samples were processed according to the methods of Hopkins D. L. & Thompson J. M. (2001) "The relationship between tenderness, proteolysis, muscle contraction and dissociation of actomyosin." *Meat Science* 57, 1-12, and a Lloyd LRX machine was used to measure 5-6 1 cm$^3$ sub-samples from each 65 g LL sample.

(iv) Intramuscular Fat Measurement

IMF samples were freeze dried and the IMF content was determined using a near infrared procedure (as described in Perry D., Shorthose W. R., Ferguson D. M. & Thompson J. M. (2001) "Methods used in the CRC program for the determination of carcass yield and beef quality." pp. 953-7).

Results

The number of measurements and simple statistics are shown in Table 1. A supplier was used to source a large range of carcases, representative of what would be typical in the Australian lamb industry. Carcases ranged from 14-32 kg with 3.5 to 33.0 mm fat at the GR site, with an average carcase weight of 21 kg and average fatness of 12.2 mm. Likewise, IMF, SF5, fresh colour and pHu reflected normal industry ranges.

The range in carcass and eating quality parameters provided a source for proof of concept of meat eating quality solutions analysis.

TABLE 1

Statistics of lambs measured at PVP.

| Variable | N | Mean | SD | Min | Max |
| --- | --- | --- | --- | --- | --- |
| HCWT (kg) | 200 | 21.3 | 3.15 | 14.3 | 31.8 |
| GRFAT (mm) | 200 | 12.2 | 5.52 | 3.5 | 33.0 |
| CFAT (mm) | 197 | 4.7 | 2.910 | 0.21 | 17.38 |
| EMW (mm) | 199 | 66.80 | 5.332 | 52.33 | 81.36 |
| EMD (mm) | 199 | 31.52 | 4.516 | 18.01 | 45.94 |
| EMA (mm$^2$) | 199 | 16.89 | 3.048 | 9.29 | 25.80 |
| L* | 200 | 35.8 | 2.95 | 29.1 | 42.5 |
| a* | 200 | 14.8 | 2.36 | 10.3 | 21.0 |
| b* | 200 | 5.1 | 1.57 | 1.5 | 9.6 |
| pHLL | 198 | 5.73 | 0.112 | 5.50 | 6.20 |
| pHtemp | 198 | 6.1 | 1.73 | 3.1 | 8.7 |
| SF5 (N) | 200 | 48.29 | 13.210 | 21.96 | 93.15 |
| IMF (%) | 199 | 4.60 | 0.963 | 2.21 | 7.55 |

EXAMPLE 2

Acquisition of Data, and Processing of Measurements Taken Using a Probe (a) Summary This example describes the results of data processing of measurements taken using a fibre probe.

Both linear and categorical statistical approaches were employed in the analysis.

Analysis of the data was used to determine one or more parameters indicative of quality of the meat product, and thereby assess the quality of the meat product on the basis of those one or more parameters.

Of the parameters investigated, it was found that meat quality measures of IMF (intramuscular fat) and SF (shear force) could be predicted statistically significantly using both modeling approaches.

It was also found that knowledge of the state of the meat at the time of measurement improves modeling, as the spectra changes on the condition of the meat.

Based on this data it is apparent that a measurement of surrogates of meat quality can be obtained at line speed.

(b) Data Acquisition

Spectral data measurements were taken using the optical apparatus 38 of FIG. 1.

The fibre probe 16 was inserted into each of the 200 lamb carcasses, the laser 14 was activated to apply incident light to the carcass via the probe 16 and the spectrometer 24 generated spectral data representative of the autofluorescence excited in the lamb carcass. Twelve to twenty samples were taken for each carcass, and this was repeated at different temperatures, so that a hot data set, chilled data set and cold data set were obtained.

The spectral data was then processed as follows, to reduce the complexity of the data and increase prediction accuracy:

1. Data was imported from the spectrometer 24 as .txt files.
2. Data clearing was performed to remove saturated spectra. Spectra that had sharp edges and flat peaks were removed from the analysis. The detection of the saturated data was done by a series of cutoff exclusions.
3. Spectral data below 440 nm was cut off to remove laser background.
4. Multiple spectra for each sample were averaged to get one spectrum per sample.
5. All spectra were normalised to eliminate laser intensity fluctuations. The average spectra were normalised to local maxima.
6. Each ten data points were averaged to reduce the number of response variables in a set (i.e. binning the wavelengths).

Figure 5:
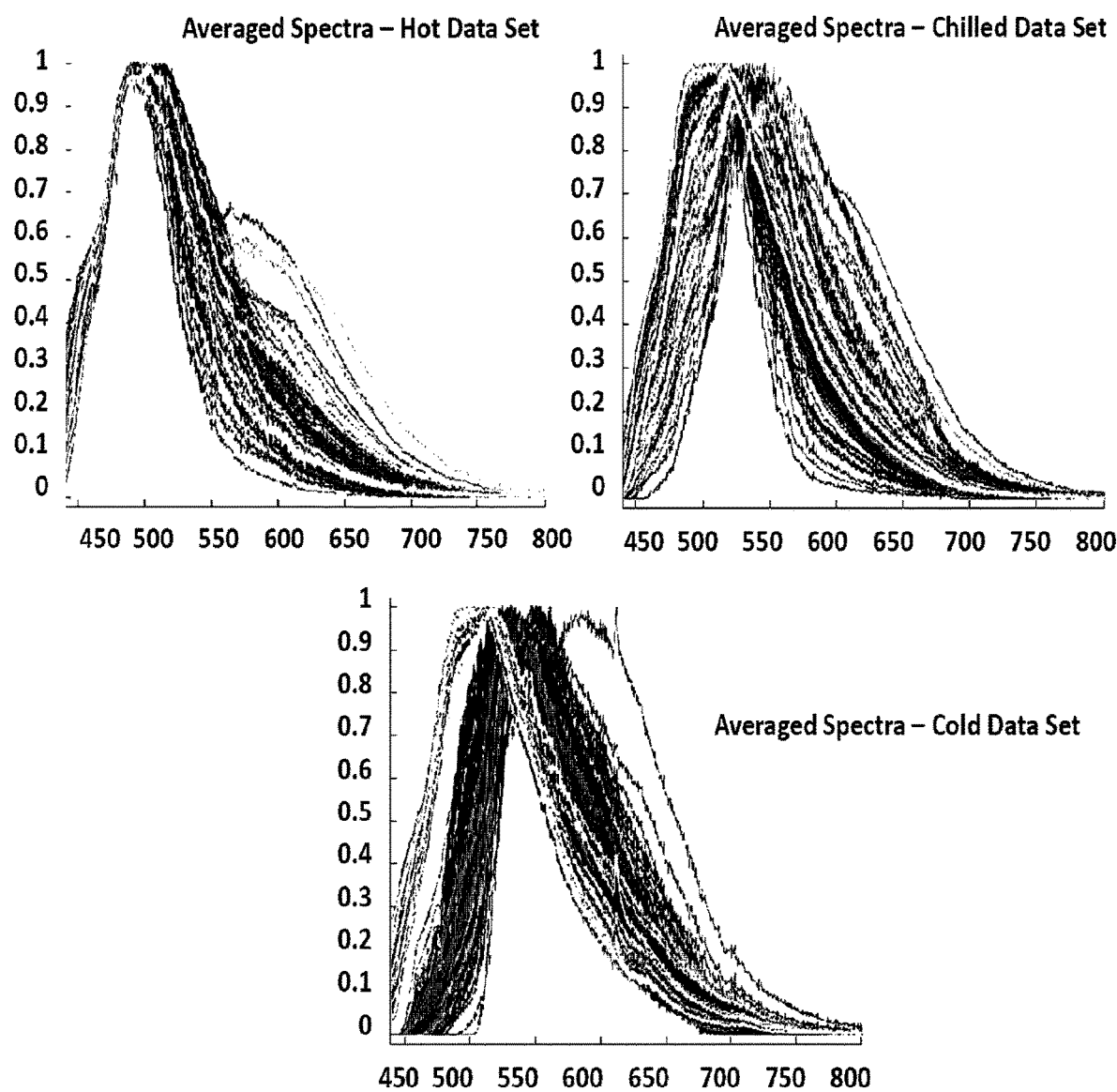
FIG. 5 shows graphs showing spectral data representative of autofluoresence excited in a meat product by the application of laser light to the meat product according to one embodiment.

Examples of the processed spectral data at hot, chilled and cold temperatures obtained after processing described in points 1 to 5 above are shown in FIGS. 5A-5C.

(c) Modelling

Predictor variables: The following external parameters were considered as predictor variables in the analysis:

1. HCWT—hot carcass weight;
2. GRfat—a measure of tissue depth over the 12th rib (mainly fat);
3. EMW—eye muscle width;
4. EMD—eye muscle depth;
5. FatC—the amount of fat over the eye muscle;
6. EMA—eye muscle area;
7. pHu_loin—the pH of the eye muscle;
8. pHu_temp—the temperature of the eye muscle at the time of measuring the pHu;
9. L—measure of colour lightness;
10. a—measure of colour redness;
11. b—measure of colour yellowness;
12. SF—shear force;
13. IMF—intra-muscular fat.

The studies identified SF and IMF as two measures of importance to meat quality.

Methods

Initially two methods were used to find correlation between all of the external parameters and the response variables (spectral data): 1) linear model with Akaike's Information Criterion, and 2) k-fold Cross Validation. Each of the methods provided a number of output parameters that were used to estimate how well the model described the data. Those output parameters included:

Residual Standard Error (RSE)—measure of quality of the linear regression fit. Any prediction would still be off by that amount.

R-squared—measure of how the model fits the actual data. Value between 0 and 1, where higher values would correspond to better fit.

Adjusted R-square—adjusted for the number of variables.

F-Statistic—indicated whether there was a relationship between our predictor (external parameters) and response variables (spectral data). Should be much larger than 1.

p-value—tested the null-hypothesis (that predictor variables have no effect on response). Have to be smaller than 0.005 to be able to reject the null hypothesis (to say that the relationship exists). In the figures, log 10(p-value) was plotted for better visual representation of the values.

The results of this analysis created a model that allowed for the estimation of a continuous variable for the prediction score. That is a value+/−an error rate was returned by the optimal model.

An alternative categorical approach was also applied using machine learning which fragmented the dataset into categorical gradings for each variable. For example, IMF scores of 2-3 were categorised B, 3-4 were C etc. Thus a measurement was provided that allowed categorisation rather than quantification of measurements.

Summary of the Linear Model Results

FIGS. 6 to 9, present the output parameters of the statistical model. pHu_temp predictor was excluded from the analysis as this variable varied in steps and was found to produce artificial statistical output. Moreover, this parameter was physically irrelevant to the spectral response variable considered in the analysis.

Figure 6:
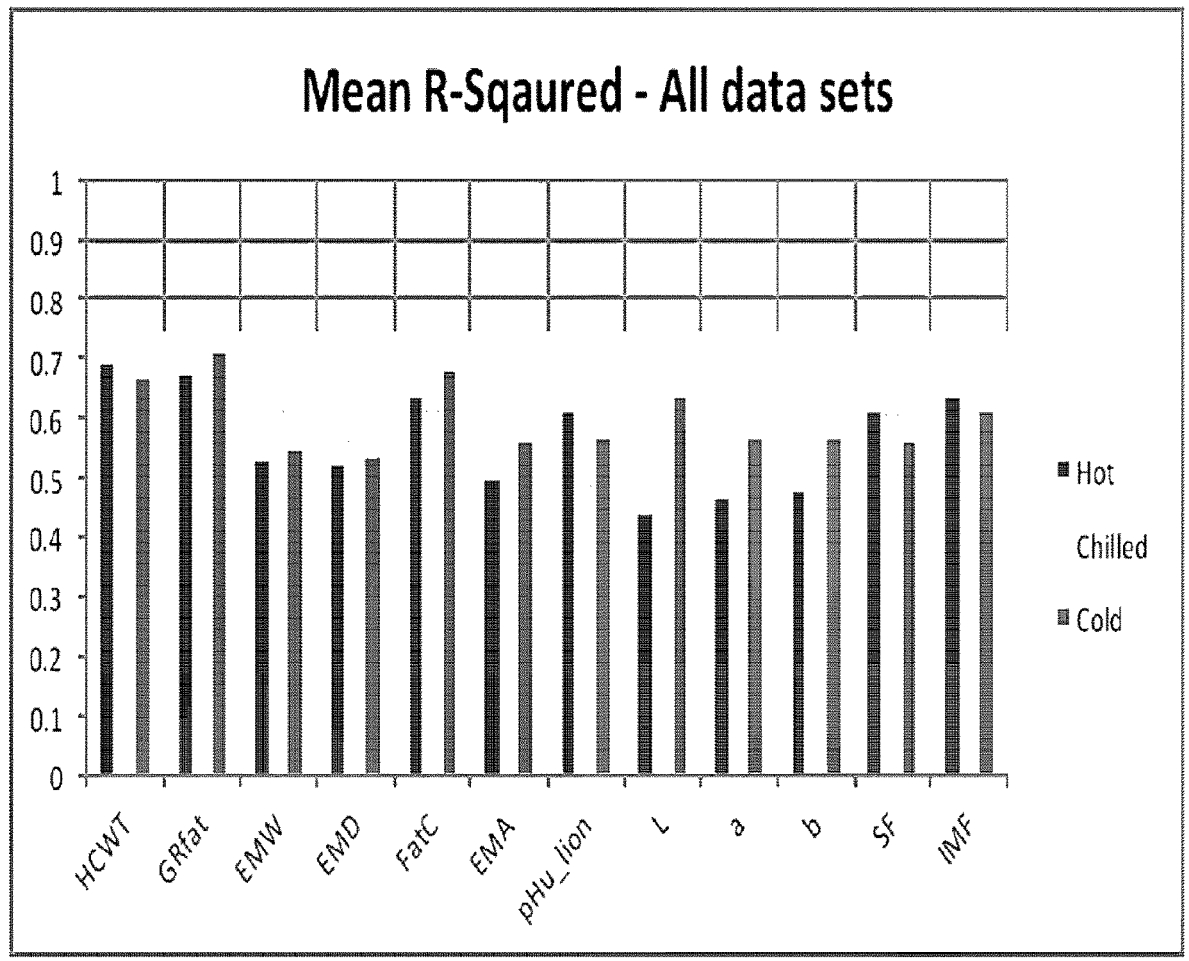
FIG. 6 shows mean R-squared values for all data sets, averaged across three methods: linear model, Akaike's Information Criterion, and 5-fold Cross Validation.

FIG. 6 shows the mean R-squared values for all data sets, averaged across three methods: linear model, Akaike's Information Criterion, and 5-fold Cross Validation.

Considering the R-squared and Adjusted R-squared values, the following predictor variables showed better results relative to the other parameters: HCWT, GRfat, FatC, SF, and IMF. This was relatively consistent across all three data sets, however, lightness parameter, L, appeared to have better R-squared value for the Cold data set. pHu_loin parameter showed higher Adjusted R-squared value for the Hot data set.

F-Statistic values were almost twice as large for the same parameters: HCWT, GRfat, FatC, SF, and IMF, and smaller p-values were attributed to the same parameters. Here, the lightness parameter, L, also showed better statistics for the Cold data set, while pHu_loin parameter showed better values for Hot data set.

Figure 7:
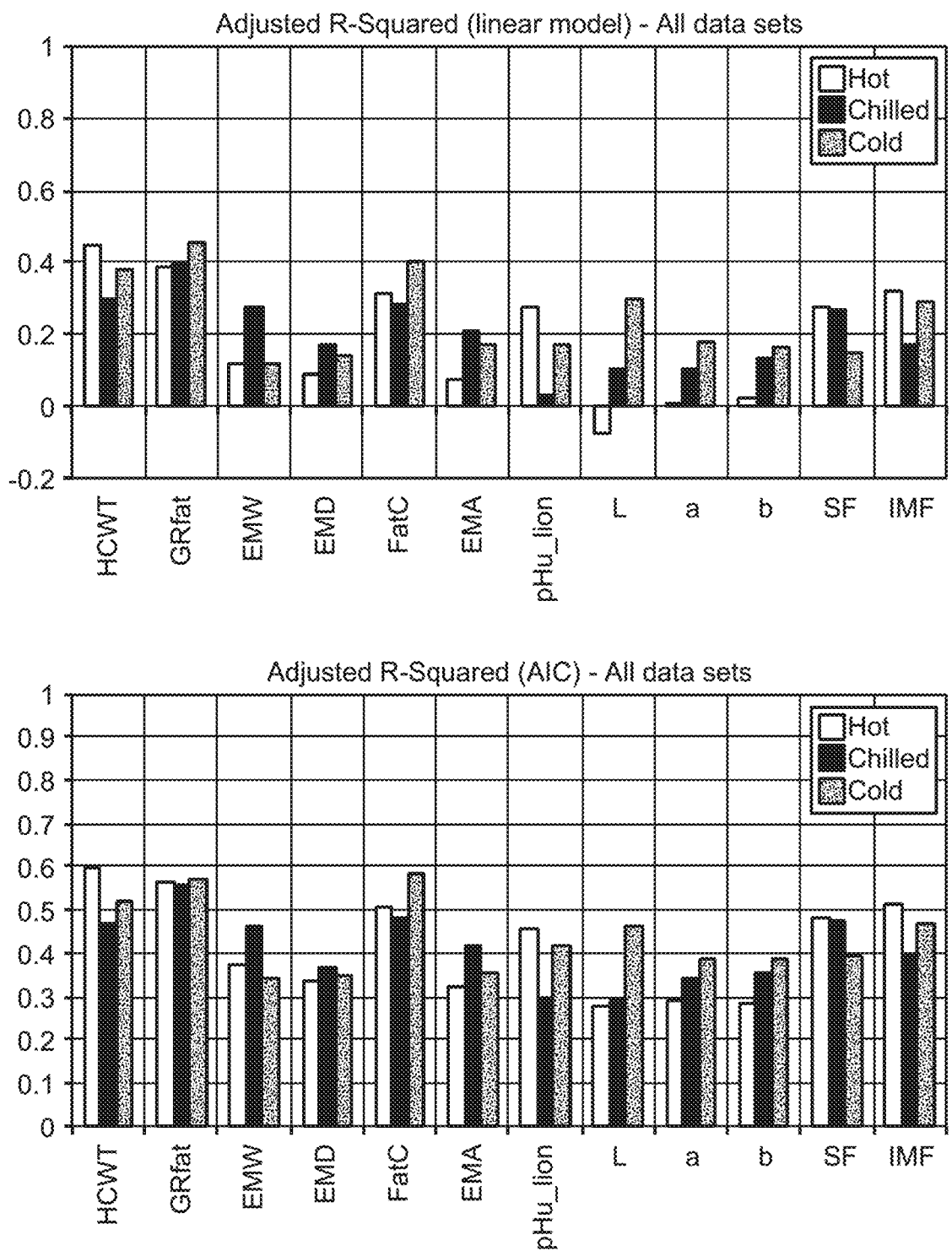
FIG. 7 shows adjusted R-squared values for all data sets for linear model and Akaike's Information Criterion.

FIG. 7 shows adjusted R-squared values for all data sets for linear model and Akaike's Information Criterion.

Figure 8:
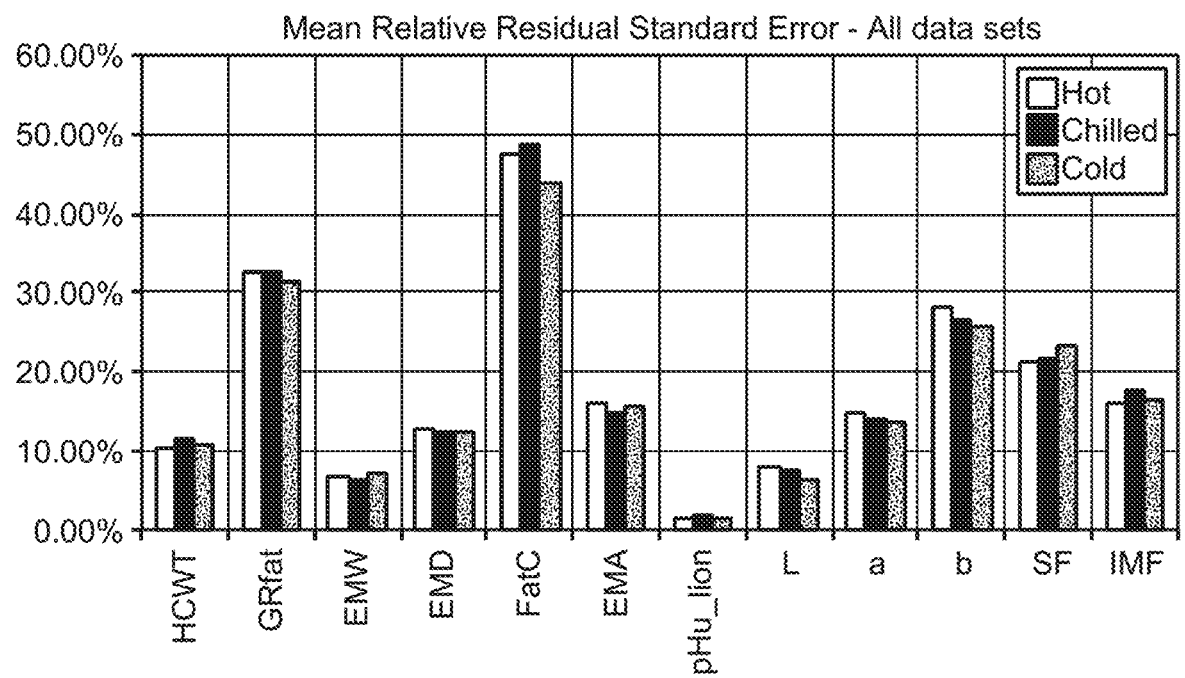
FIG. 8 shows mean Relative Residual Standard Error for all data sets averaged across linear model and AIC; and F-Statistic values for all data sets for linear model.
Figure 8:
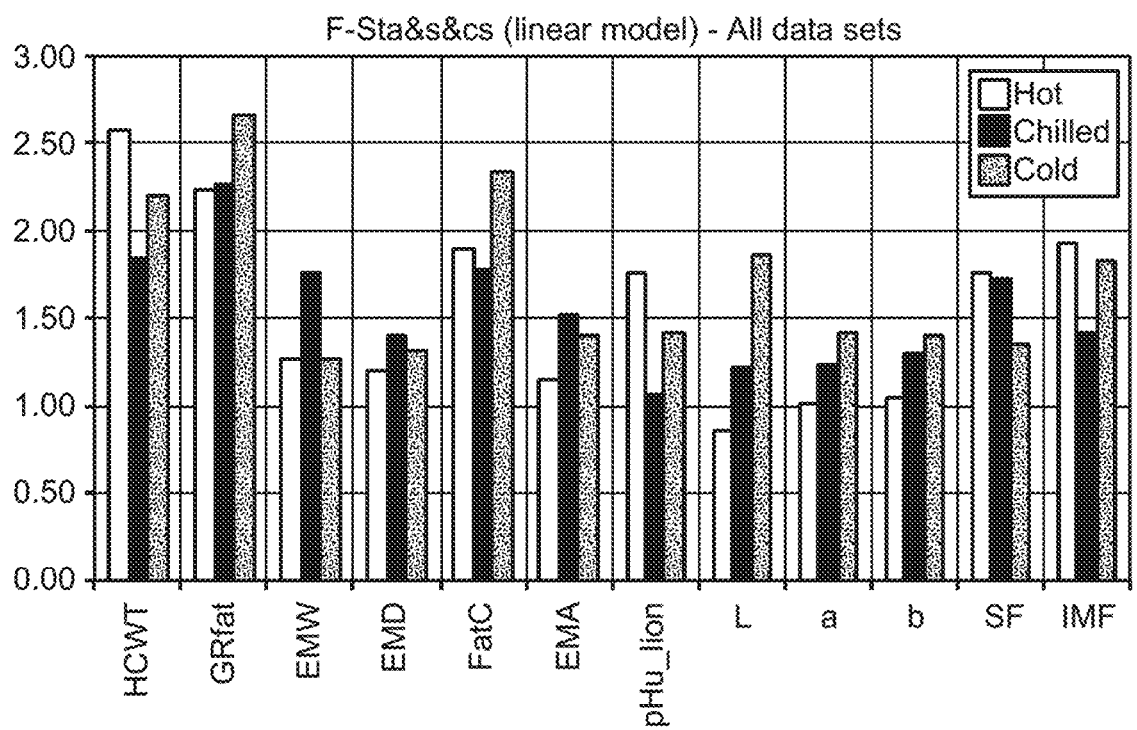

FIG. 8 shows mean Relative Residual Standard Error for all data sets averaged across linear model and AIC; and F-Statistic values for all data sets for linear model. Values much larger than 1 (shown in black line) indicate there is relationship between predictor and response variables.

Figure 9:
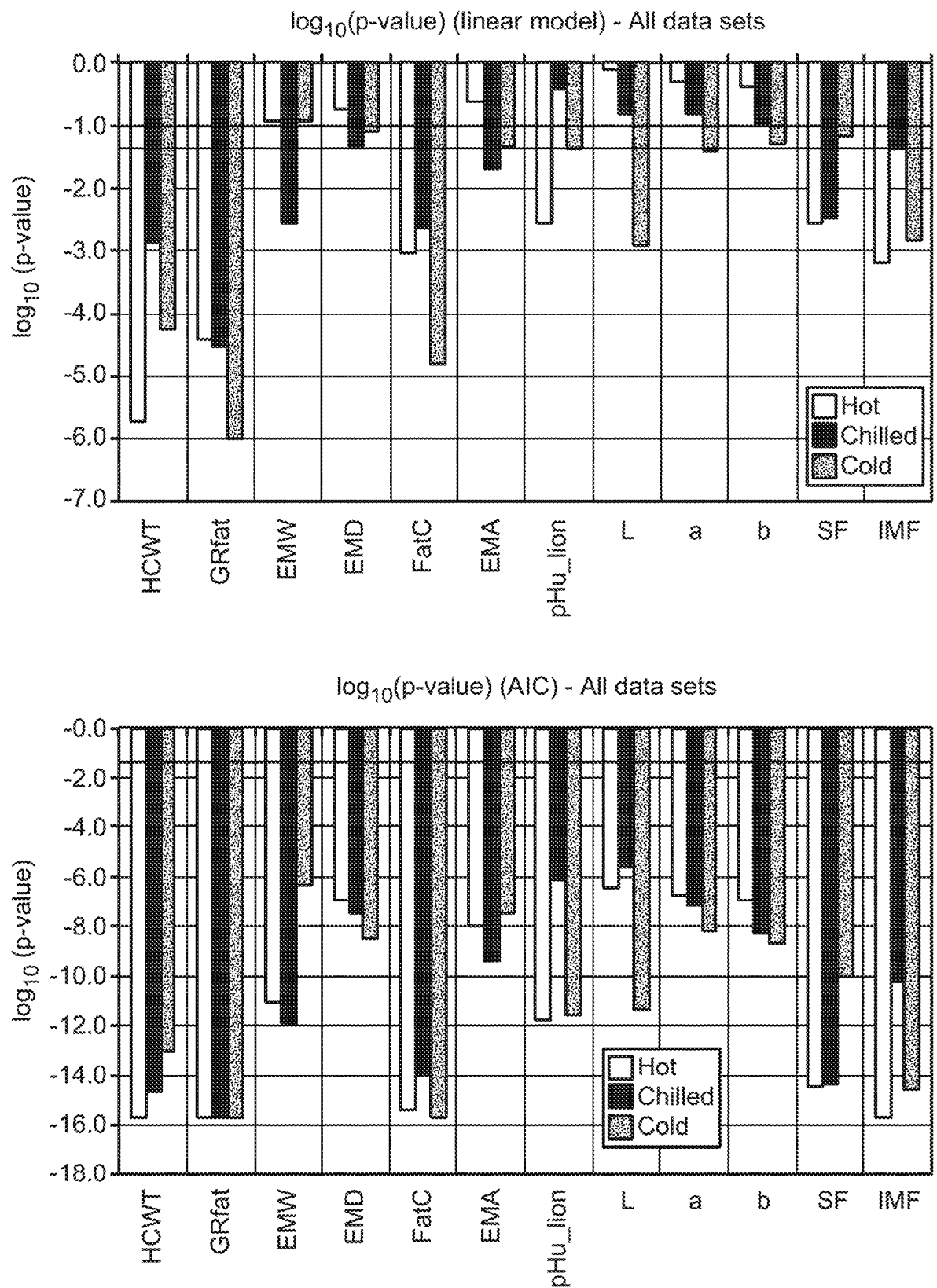
FIG. 9 shows log 10(p-value) for all data sets for linear model and Akaike's Information Criterion.

FIG. 9 shows $\log_{10}$(p-value) for all data sets for linear model and Akaike's Information Criterion. Values below the threshold of $\log_{10}(0.05)=-1.3$ indicate that we can reject the null hypothesis, and a relationship between predictor and response variables exists.

Summary of the Categorical Model Results

Analysis incorporating categorical statistical approaches allowed greater collecting of the data, such that all hot, chilled and cold measurements were analysed together, with a categorical assignment of their measurement temperature. The data set was randomly split into an 80:20/build:test set to allow independent validation of the model. A parallel assessment of 5 different types of machine learning approaches was performed with the best selected in a head to head test. For SF K nearest neighbour approach created the best predictive model with an accuracy of 96.6% in the test dataset. That is, out of 33 C grading's of SF the model incorrectly assigned 1 as a D.

| Confusion Matrix and Statistics | | | | | | | |
|---|---|---|---|---|---|---|---|
| Reference | | | | | | | |
| Prediction | A | B | C | D | E | F | G |
| A | 6 | 0 | 0 | 0 | 0 | 0 | 0 |
| B | 0 | 30 | 0 | 0 | 0 | 0 | 0 |
| C | 0 | 0 | 32 | 1 | 0 | 0 | 0 |
| D | 0 | 0 | 1 | 27 | 1 | 0 | 0 |
| E | 0 | 0 | 0 | 0 | 11 | 0 | 0 |
| F | 0 | 0 | 0 | 0 | 0 | 7 | 1 |
| G | 0 | 0 | 0 | 0 | 0 | 0 | 0 |

Overall Statistics

Accuracy: 0.9658
95% CI: (0.9148, 0.9906)
No Information Rate: 0.2821
P-Value [Acc > NIR]: <2.2e−16
Kappa: 0.9561
Mcnemar's Test P-Value: NA

| Statistics by Class: | | | | | | | |
|---|---|---|---|---|---|---|---|
| | Class: A | Class: B | Class: C | Class: D | Class: E | Class: F | Class: G |
| Sensitivity | 1.00000 | 1.0000 | 0.9697 | 0.9643 | 0.91667 | 1.00000 | 0.000000 |
| Specificity | 1.00000 | 1.0000 | 0.9881 | 0.9775 | 1.00000 | 0.99091 | 1.000000 |

-continued

| Confusion Matrix and Statistics | | | | | | | |
|---|---|---|---|---|---|---|---|
| Pos Pred Value | 1.00000 | 1.0000 | 0.9697 | 0.9310 | 1.00000 | 0.87500 | NaN |
| Neg Pred Value | 1.00000 | 1.0000 | 0.9881 | 0.9886 | 0.99057 | 1.00000 | 0.991453 |
| Prevalence | 0.05128 | 0.2564 | 0.2821 | 0.2393 | 0.10256 | 0.05983 | 0.008547 |
| Detection Rate | 0.05128 | 0.2564 | 0.2735 | 0.2308 | 0.09402 | 0.05983 | 0.000000 |
| Detection Prevalence | 0.05128 | 0.2564 | 0.2821 | 0.2479 | 0.09402 | 0.06838 | 0.000000 |
| Balanced Accuracy | 1.00000 | 1.0000 | 0.9789 | 0.9709 | 0.95833 | 0.99545 | 0.500000 |

For IMF, the head to head test yielded a 94.7% accuracy using a random forest approach.

| Confusion Matrix and Statistics | | | | | | | | | | | | |
|---|---|---|---|---|---|---|---|---|---|---|---|---|
| | Reference | | | | | | | | | | | |
| Prediction | A | B | C | D | E | F | G | H | I | J | K | L |
| A | 0 | 0 | 0 | 0 | 0 | 0 | 0 | 0 | 0 | 0 | 0 | 0 |
| B | 0 | 0 | 1 | 0 | 0 | 0 | 0 | 0 | 0 | 0 | 0 | 0 |
| C | 0 | 1 | 7 | 0 | 0 | 0 | 0 | 0 | 0 | 0 | 0 | 0 |
| D | 0 | 0 | 2 | 21 | 0 | 0 | 0 | 0 | 0 | 0 | 0 | 0 |
| E | 0 | 0 | 0 | 0 | 24 | 2 | 0 | 0 | 0 | 0 | 0 | 0 |
| F | 0 | 0 | 0 | 0 | 0 | 21 | 0 | 0 | 0 | 0 | 0 | 0 |
| G | 0 | 0 | 0 | 0 | 0 | 0 | 16 | 0 | 0 | 0 | 0 | 0 |
| H | 0 | 0 | 0 | 0 | 0 | 0 | 0 | 8 | 0 | 0 | 0 | 0 |
| I | 0 | 0 | 0 | 0 | 0 | 0 | 0 | 0 | 5 | 0 | 0 | 0 |
| J | 0 | 0 | 0 | 0 | 0 | 0 | 0 | 0 | 0 | 5 | 0 | 0 |
| K | 0 | 0 | 0 | 0 | 0 | 0 | 0 | 0 | 0 | 0 | 0 | 0 |
| L | 0 | 0 | 0 | 0 | 0 | 0 | 0 | 0 | 0 | 0 | 0 | 0 |

Overall Statistics

Accuracy: 0.9469
95% CI: (0.888, 0.9803)
No Information Rate: 0.2124
P-Value [Acc > NIR]: <2.2e−16
Kappa: 0.9368
Mcnemar's Test P-Value: NA Statistics by Class:

| | Class: A | Class: B | Class: C | Class: D | Class: E | Class: F | Class: G | Class: H | Class: I | Class: J | Class: K | Class: L |
|---|---|---|---|---|---|---|---|---|---|---|---|---|
| Sensitivity | NA | 0.00000 | 0.70000 | 1.0000 | 1.0000 | 0.9130 | 1.0000 | 1.0000 | 1.00000 | 1.00000 | NA | NA |
| Specificity | 1 | 0.99107 | 0.99029 | 0.9783 | 0.9775 | 1.0000 | 1.0000 | 1.0000 | 1.00000 | 1.00000 | 1 | 1 |
| Pos Pred Value | NA | 0.00000 | 0.87500 | 0.9130 | 0.9231 | 1.0000 | 1.0000 | 1.0000 | 1.00000 | 1.00000 | NA | NA |
| Neg Pred Value | NA | 0.99107 | 0.97143 | 1.0000 | 1.0000 | 0.9783 | 1.0000 | 1.0000 | 1.00000 | 1.00000 | NA | NA |
| Prevalence | 0 | 0.00885 | 0.08850 | 0.1858 | 0.2124 | 0.2035 | 0.1416 | 0.0708 | 0.04425 | 0.04425 | 0 | 0 |
| Detection Rate | 0 | 0.00000 | 0.06195 | 0.1858 | 0.2124 | 0.1858 | 0.1416 | 0.0708 | 0.04425 | 0.04425 | 0 | 0 |
| Detection Prevalence | 0 | 0.00885 | 0.07080 | 0.2035 | 0.2301 | 0.1858 | 0.1416 | 0.0708 | 0.04425 | 0.04425 | 0 | 0 |
| Balanced Accuracy | NA | 0.49554 | 0.84515 | 0.9891 | 0.9888 | 0.9565 | 1.0000 | 1.0000 | 1.00000 | 1.00000 | NA | NA |

OBSERVATIONS AND CONCLUSIONS

R-squared: Overall, the R-squared values were relatively low, even for the fat-related parameters, and were around 0.6, with the adjusted R-squared values expectedly lower. Akaike's Information Criterion resulted in an improved model once the best fitting response variables were left in the model. On average, 30-50% of the initial response variables were left after AIC was applied. The k-fold Cross Validation method showed similar R-squared values to the linear model, or the AIC.

Number of response variables: When reducing the number of response variables, the overall statistical results became worse, while an increase in the number of response variables lead to the overall improvement of the statistical model. This was to be expected as it indicated that the total amount of data available to calculate the maximal model had not been reached. This confirmed that an 80/20 and kfold approach was justified. When considering the relative results in the statistical analysis, the same parameters showed better correlation than others, independent of the number of the response variables considered.

Variation in spectral data: When intervals of less variation in the spectral data were chosen instead of the most variable range, the statistical model outcome improved, even when the same number of response variables were considered.

Relative Residual Standard Errors: RSEs for the fat-related parameters were as follows: ≈10% for HCWT, ≈30% for GRfat, ≈45% for FatC, and ≈15% for IMF.

Relationship between predictor variables: Analysis of the correlation between predictor variables themselves revealed there were internal correlations between several parameters. For example, Table 2 shows the statistical output of the linear models created based on relationship between some external parameters.

TABLE 2

Statistical relationship between external parameters.

| Model | R2 | Adjusted $R^2$ | F statistic | p-value |
|---|---|---|---|---|
| HCWT~GRfat | 0.467 | 0.464 | 173.50 | 2.20E−16 |
| HCWT~FatC | 0.274 | 0.270 | 74.56 | 1.94E−15 |
| HCWT~pHu_loin | 0.117 | 0.112 | 26.12 | 7.54E−07 |
| HCWT~IMF | 0.019 | 0.014 | 3.77 | 5.36E−02 |
| GRfat~FatC | 0.491 | 0.488 | 190.80 | 2.20E−16 |

TABLE 2-continued

Statistical relationship between external parameters.

| Model | R2 | Adjusted $R^2$ | F statistic | p-value |
|---|---|---|---|---|
| HCWT~(GRfat + FatC + pHu_loin + IMF) | 0.694 | 0.674 | 35.31 | 2.20E−16 |

Linear model conclusions: The models created for the following parameters were shown to be more statistically significant when compared to other analysed parameters: HCWT, GRfat, FatC, SF and IMF. Some internal relationship between those parameters can also be assumed. Thus there exists a model that can statistically significantly predict HCWT, GRfat, FatC, SF and IMF. Albeit each model being different.

Categorical model conclusions: The increased accuracy of the categorical approach was proportional to the loss of information gained in the linear model.

Overall conclusions: It would appear that a statistically significant model predicting meat quality surrogate measures using a fibre based approach collected at line speed is possible.

Further data is provided in Appendices A and B, provided below.

APPENDIX A—EXTERNAL PARAMETERS OF MEAT QUALITY (TABLE 3)

TABLE 3

External parameters of meat quality

| ID | HCWT | GRfat | EMW | EMD | FatC | EMA | pHu loin | pHu temp | L* | a* | b* | SF | IMF |
|---|---|---|---|---|---|---|---|---|---|---|---|---|---|
| 1 | 25.9 | 21.0 | 65.72 | 31.21 | 9.6 | 16.41 | 5.71 | 4.8 | 32.49 | 16.83 | 5.85 | 42.04 | 5.7 |
| 2 | 21.7 | 10.5 | 62.02 | 32.39 | 3.43 | 16.07 | 5.75 | 4.5 | 33.51 | 16.74 | 6.12 | 36.00 | 5.10 |
| 3 | 24.2 | 16.5 | 66.1 | 32.6 | 4.5 | 17.24 | 5.61 | 4.7 | 39.79 | 11.58 | 2.8 | 36.02 | 6.62 |
| 4 | 25.1 | 20.0 | 67.97 | 39.74 | 6.27 | 21.61 | 5.6 | 5.6 | 34.7 | 12.52 | 3.32 | 41.35 | 5.12 |
| 5 | 17.7 | 7.0 | 73.02 | 28.5 | 2.78 | 16.65 | 5.8 | 4.5 | 35.03 | 13.92 | 4 | 52.76 | 4.05 |
| 6 | 27.6 | 14.5 | 75.53 | 42.69 | 3.85 | 25.80 | 5.64 | 4.5 | 34.87 | 15.66 | 5.41 | 37.07 | 5.32 |
| 7 | 16.6 | 7.5 | 64.62 | 32.03 | 2.88 | 16.57 | 5.87 | 4.8 | 41.11 | 12.21 | 3.61 | 33.11 | 5.43 |
| 8 | 24.8 | 19.5 | 72.53 | 32.68 | 5.06 | 18.96 | 5.63 | 4.5 | 39.8 | 10.26 | 1.52 | 26.90 | 4.02 |
| 9 | 21.9 | 13.0 | 60.53 | 29.09 | 5.72 | 14.09 | | | 38.86 | 11.61 | 3.34 | 32.18 | 6.97 |
| 10 | 24.4 | 15.5 | 67.04 | 36.49 | 4.35 | 19.57 | 5.64 | 4.5 | 32.57 | 15.46 | 4.51 | 52.68 | 5.70 |
| 11 | 16.8 | 11.5 | 58.22 | 27.65 | 2.61 | 12.88 | 5.64 | 4.5 | 33.08 | 16.98 | 5.4 | 55.42 | 5.61 |
| 12 | 24.3 | 15.5 | 66.67 | 33.74 | 3.46 | 18.00 | 5.64 | 4.5 | 39.07 | 12.33 | 3.2 | 43.58 | 4.27 |
| 13 | 20.9 | 18.5 | 64.5 | 18.01 | 8.9 | 9.29 | 5.75 | 4.1 | 42.09 | 14.52 | 5.39 | 49.27 | 6.95 |
| 14 | 18.1 | 8.0 | 62.03 | 32.81 | 3.29 | 16.28 | 5.93 | 4.1 | 39.52 | 12.13 | 3.22 | 41.80 | 4.29 |
| 15 | 23.2 | 23.0 | 60.35 | 30.43 | 15.63 | 14.69 | 5.97 | 5.2 | 34.64 | 18.06 | 7.73 | 47.46 | 7.55 |
| 16 | 27.8 | 22.0 | 67.19 | 39.29 | 17.23 | 21.12 | 5.67 | 4.5 | 39.87 | 12.84 | 4.28 | 21.96 | 4.99 |
| 17 | 23.7 | 21.5 | 61.8 | 34.1 | 3.34 | 16.86 | 5.64 | 4.1 | 30.03 | 14.86 | 4.61 | 39.28 | 4.86 |
| 18 | 23.5 | 19.5 | 63.72 | 27.74 | 8.5 | 14.14 | 5.71 | 3.8 | 30.46 | 16.23 | 4.78 | 34.97 | 3.99 |
| 19 | 21.3 | 15.5 | 58.65 | 36.03 | 4.44 | 16.91 | 5.85 | 3.5 | 33.66 | 19.58 | 8.36 | 42.24 | 5.31 |
| 20 | 21.3 | 13.5 | 58.97 | 36.03 | 2.74 | 17.00 | 5.95 | 3.3 | 36.89 | 13.38 | 4.14 | 40.21 | 5.59 |
| 21 | 18.1 | 11.0 | 63.66 | 26.37 | 3.25 | 13.43 | 5.92 | 3.8 | 30.48 | 17.63 | 6.69 | 40.66 | 4.98 |
| 22 | 29.4 | 23.5 | 68.32 | 38.12 | 10.32 | 20.83 | 5.77 | 3.6 | 31.51 | 16.9 | 5.82 | 38.48 | 4.30 |
| 23 | 20.2 | 11.0 | 64.29 | 30.75 | 4.31 | 15.82 | 5.81 | 3.2 | 35.86 | 12.67 | 3.59 | 35.21 | 5.28 |
| 24 | 31.8 | 30.0 | 75.13 | 36.98 | 6.27 | 22.23 | 5.62 | 4.4 | 34.3 | 16.73 | 6.65 | 30.77 | 4.85 |
| 25 | 29.3 | 30.0 | 71.29 | 39.11 | 12.95 | 22.31 | 5.57 | 4.1 | 37.19 | 14.01 | 4.28 | 34.82 | 6.15 |
| 26 | 24.5 | 12.5 | 75.5 | 25.04 | 9.43 | 15.12 | 5.67 | 4.1 | 37.29 | 13.32 | 4.58 | 34.94 | 5.59 |
| 27 | 19.1 | 12.5 | 63.86 | 28.99 | 4.57 | 14.81 | 5.84 | 3.4 | 36.83 | 14.87 | 4.68 | 38.18 | 6.12 |
| 28 | 27 | 15.5 | 76.22 | 33.27 | 11.89 | 20.29 | 5.74 | 3.5 | 38.25 | 11.15 | 2.48 | 37.02 | 4.40 |
| 29 | 25.2 | 29.0 | 71.73 | 32.03 | 10.25 | 18.38 | 5.6 | 3.7 | 34.02 | 19.14 | 7.75 | 41.42 | 6.06 |
| 30 | 18.5 | 6.5 | 62.99 | 28.33 | 8.95 | 14.28 | 5.84 | 3.6 | 31.78 | 15.69 | 5.48 | 41.86 | 4.60 |
| 31 | 19.4 | 6.5 | 63.38 | 28.07 | 3.48 | 14.23 | 5.88 | 3.3 | 34.14 | 15.2 | 5.08 | 54.92 | 5.78 |
| 32 | 21.3 | 10.0 | 68.35 | 28.98 | 3.3 | 15.85 | 5.69 | 3.7 | 34.93 | 13.94 | 4.39 | 53.28 | 5.31 |
| 33 | 20.8 | 17.5 | 62.68 | 27.51 | 9.27 | 13.79 | 5.94 | 4.1 | 38.25 | 13.73 | 4.17 | 29.31 | 4.40 |
| 34 | 16.2 | 7.5 | 55.75 | 34.03 | 2.64 | 15.18 | 5.74 | 3.3 | 31.12 | 18.59 | 6.64 | 38.66 | 4.66 |
| 35 | 26.2 | 17.5 | 76.38 | 41.29 | | 25.23 | 5.75 | 3.2 | 32.23 | 17.77 | 6.83 | 33.98 | 4.48 |
| 36 | 19.4 | 8.5 | 70.74 | 34.81 | 2.45 | 19.70 | 5.61 | 4.5 | 36.89 | 12.71 | 3.19 | 60.04 | 4.03 |
| 37 | 20.4 | 12.0 | 70.01 | 29.31 | 4.48 | 16.42 | 5.64 | 3.7 | 38.19 | 11.85 | 3.37 | 37.09 | 4.75 |
| 38 | 19.7 | 15.0 | 67.05 | 31.47 | 7.43 | 16.88 | 5.79 | 4.1 | 40.65 | 10.83 | 2.93 | 40.39 | 4.46 |
| 39 | 21.4 | 11.5 | 69.05 | 32.38 | 7.51 | 17.89 | 5.83 | 4.2 | 32.5 | 14.96 | 4.46 | 48.47 | 4.14 |

TABLE 3-continued

External parameters of meat quality

| ID | HCWT | GRfat | EMW | EMD | FatC | EMA | pHu loin | pHu temp | L* | a* | b* | SF | IMF |
|---|---|---|---|---|---|---|---|---|---|---|---|---|---|
| 40 | 14.3 | 5.0 | 61 | 27.93 | 1.28 | 13.63 | 6.03 | 4.5 | 31.25 | 16.08 | 4.99 | 38.65 | 4.48 |
| 41 | 19.4 | 12.5 | 63.34 | 28.82 | 4.85 | 14.60 | 5.68 | 4.2 | 36.03 | 14.31 | 4.9 | 32.98 | 5.41 |
| 42 | 21.3 | 14.5 | 64.47 | 27.38 | 5.24 | 14.11 | 5.68 | 4.5 | 38.74 | 16.72 | 7.1 | 29.34 | 7.15 |
| 43 | 20.7 | 11.5 | 66.31 | 32.48 | 4.53 | 17.23 | 6.2 | 4.2 | 38.89 | 12.14 | 3.49 | 23.74 | 4.57 |
| 44 | 22.9 | 12.0 | 77.82 | 28.07 | 6.57 | 17.48 | 5.7 | 4.5 | 30.88 | 14.41 | 4.59 | 62.45 | 4.00 |
| 45 | 19.5 | 12.5 | 64.1 | 24.2 | 6.77 | 12.41 | 5.59 | 4.2 | 32.55 | 17.37 | 6.45 | 41.92 | 4.86 |
| 46 | 18.7 | 9.0 | 58.5 | 28.87 | 4.17 | 13.51 | 5.92 | 4.1 | 34.59 | 16.11 | 5.98 | 42.75 | 4.59 |
| 47 | 18.2 | 12.5 | 59.21 | 29.01 | 5.27 | 13.74 | 5.89 | 4.5 | 33.31 | 17.04 | 6.6 | 36.75 | 5.11 |
| 48 | 17.6 | 10.5 | 54.56 | 29.25 | 3.06 | 12.77 | 6.02 | 4.1 | 36.03 | 14.08 | 5.01 | 30.68 | 5.02 |
| 49 | 20.1 | 11.5 | 66.18 | 29.17 | 2.06 | 15.44 | 5.73 | 4 | 40.42 | 11.74 | 3.12 | 37.09 | 5.24 |
| 50 | 23.1 | 16.5 | 62.62 | 30.48 | 5.58 | 15.27 | 5.65 | 4.1 | 41.01 | 12.66 | 3.79 | 39.53 | 5.27 |
| 51 | 21.7 | 17.5 | 71.3 | 30.9 | 6.21 | 17.63 | 5.69 | 3.8 | 34.06 | 15.3 | 4.94 | 59.62 | |
| 52 | 20 | 15.0 | 64.73 | 31.56 | 4.29 | 16.34 | 5.69 | 4.1 | 36.6 | 13.57 | 3.99 | 38.13 | 5.88 |
| 53 | 15.8 | 4.5 | 61.52 | 30.85 | 0.75 | 15.18 | 5.89 | 4.8 | 29.84 | 16.26 | 5.16 | 53.81 | 4.10 |
| 54 | 23.5 | 15.0 | 69.35 | 30.88 | 5.96 | 17.13 | 5.57 | 3.5 | 36.01 | 12.82 | 3.57 | 33.01 | 4.09 |
| 55 | 27.2 | 33.0 | 69.16 | 35.97 | 9.5 | 19.90 | 5.68 | 3.7 | 35.87 | 16.37 | 5.83 | 37.58 | 5.76 |
| 56 | 18.4 | 10.5 | 66.14 | 34.59 | 3.79 | 18.30 | 5.98 | 3.1 | 33.67 | 14.84 | 4.82 | 45.53 | 3.97 |
| 57 | 21.3 | 12.0 | 67.78 | 35.92 | 3.82 | 19.48 | 5.81 | 3.3 | 39.47 | 10.61 | 2.63 | 42.19 | 4.53 |
| 58 | 27.3 | 24.5 | 73.47 | 31.94 | 11.98 | 18.77 | 5.66 | 3.3 | 35.16 | 13.15 | 3.54 | 48.77 | 3.91 |
| 59 | 18.9 | 14.5 | 63.67 | 33.03 | 3.02 | 16.82 | 5.88 | 3.1 | 39.57 | 13.63 | 5.31 | 44.80 | 5.45 |
| 60 | 20.7 | 18.0 | 65.08 | 27.03 | 7.02 | 14.07 | 5.78 | 3.7 | 34.49 | 16.73 | 5.92 | 28.33 | 5.16 |
| 61 | 24.3 | 10.5 | 76.44 | 34.69 | 2.6 | 21.21 | 5.8 | 3.4 | 35.43 | 11.81 | 3.15 | 53.59 | 3.35 |
| 62 | 25.4 | 12.5 | 80.52 | 38.69 | 3.86 | 24.92 | 5.66 | 3.5 | 30.65 | 16.14 | 5.02 | 47.93 | 3.18 |
| 63 | 16.4 | 7.0 | 64.35 | 29.49 | 1.75 | 15.18 | 5.74 | 3.3 | 35.46 | 12.89 | 3.65 | 51.08 | 4.99 |
| 64 | 19.7 | 10.0 | 63.01 | 24.38 | 6.16 | 12.29 | 5.68 | 3.3 | 33.19 | 15.01 | 4.6 | 28.32 | 4.49 |
| 65 | 16.7 | 10.0 | 60.48 | 24.89 | 3.86 | 12.04 | 5.82 | 4.4 | 30.45 | 14.66 | 3.99 | 54.11 | 4.48 |
| 66 | 21.7 | 17.5 | 60.18 | 32.77 | 6.88 | 15.78 | 5.72 | 3.6 | 39.15 | 12.7 | 4.1 | 37.95 | 6.77 |
| 67 | 23.7 | 16.0 | 70.07 | 36.01 | 8.87 | 20.19 | 5.83 | 3.6 | 33.96 | 16.79 | 5.94 | 38.75 | 5.13 |
| 68 | 22.4 | 14.5 | 67.67 | 29.96 | 8.46 | 16.22 | 5.75 | 3.5 | 29.05 | 18.56 | 6.86 | 52.44 | 4.54 |
| 69 | 23 | 11.5 | 61.95 | 27.83 | 2.69 | 13.79 | 5.69 | 3.7 | 29.23 | 18.46 | 6.73 | 46.08 | 4.65 |
| 70 | 20.3 | 14.5 | | | | | 5.65 | 7.4 | 37.52 | 14.76 | 5.54 | 26.53 | 4.67 |
| 71 | 22.6 | 14.5 | 67.78 | 25.07 | 5.25 | 13.59 | 5.75 | 6.9 | 33.96 | 14.15 | 4.61 | 46.97 | 3.57 |
| 72 | 19.5 | 12.0 | 60.7 | 31.03 | 5.73 | 15.07 | 5.68 | 6.6 | 39.91 | 15.27 | 5.58 | 41.72 | 6.05 |
| 73 | 22 | 12.5 | 66.09 | 33.47 | 5.51 | 17.70 | 5.79 | 6.1 | 34.79 | 16.52 | 6.02 | 32.21 | 4.50 |
| 74 | 16.1 | 8.5 | 69.3 | 25.39 | 2.78 | 14.08 | 5.9 | 6.5 | 34.75 | 15.22 | 4.93 | 51.93 | 5.07 |
| 75 | 22.2 | 15.0 | 72.83 | 31.39 | 3.84 | 18.29 | 5.67 | 6.3 | 37.19 | 12.53 | 3.53 | 65.53 | 4.11 |
| 76 | 23.8 | 15.0 | 67.22 | 36.15 | 6.15 | 19.44 | 5.56 | 6.1 | 37.19 | 17.33 | 7.1 | 29.09 | 4.89 |
| 77 | 29.1 | 29.0 | 61.44 | 37.21 | 17.38 | 18.29 | 5.61 | 7.2 | 30.92 | 20.93 | 9.02 | 42.35 | 6.72 |
| 78 | 22.4 | 16.5 | 65.02 | 30.23 | 3.78 | 15.72 | 5.63 | 6.7 | 35.18 | 17.83 | 7.53 | 55.78 | 4.69 |
| 79 | 19 | 10.5 | 63.56 | 30.19 | 4.37 | 15.35 | 5.85 | 6.7 | 36.21 | 16.6 | 5.99 | 33.96 | 5.11 |
| 80 | 21.3 | 7.5 | 62.14 | 33.81 | 3.51 | 16.81 | 5.73 | 6.1 | 36.83 | 14.19 | 4.62 | 40.04 | 5.41 |
| 81 | 25.2 | 7.0 | 72.17 | 35.34 | 5.08 | 20.40 | 5.82 | 6.1 | 38.77 | 13.1 | 3.73 | 30.15 | 3.97 |
| 82 | 17.7 | 14.5 | 60.14 | 29.58 | 4.07 | 14.23 | 5.68 | 6.3 | 42.24 | 14.45 | 5.24 | 31.02 | 5.54 |
| 83 | 21 | 12.0 | 66.15 | 28.44 | 5.91 | 15.05 | 5.71 | 6.3 | 38.82 | 11.57 | 3.18 | 52.59 | 6.05 |
| 84 | 28.5 | 26.0 | 71.01 | 37.14 | 10.42 | 21.10 | 5.75 | 6.7 | 33.37 | 19.17 | 7.88 | 63.53 | 4.60 |
| 85 | 22.6 | 13.5 | 61.62 | 29.85 | 3.43 | 14.71 | 5.73 | 6.2 | 31.98 | 18.55 | 6.73 | 57.21 | 4.43 |
| 86 | 19.2 | 11.5 | 59.94 | 37.43 | 6.04 | 17.95 | 5.72 | 6.2 | 31.77 | 14.91 | 4.75 | 53.36 | 3.91 |
| 87 | 20.1 | 7.0 | 62.08 | 30.62 | 2.25 | 15.21 | 5.77 | 6.2 | 36.03 | 17.5 | 6.41 | 44.35 | 3.96 |
| 88 | 20.4 | 11.5 | 65.08 | 30.77 | 3.21 | 16.02 | 5.68 | 6.1 | 34.19 | 14.49 | 4.46 | 43.08 | 3.78 |
| 89 | 20.4 | 8.0 | 68.13 | 31.49 | 2.37 | 17.16 | 5.82 | 6.2 | 34.02 | 15.51 | 5.61 | 48.95 | 3.75 |
| 90 | 21.6 | 8.0 | 66.38 | 30.13 | 2.74 | 16.00 | 5.83 | 6.2 | 37.87 | 14.89 | 5.55 | 36.45 | 6.53 |
| 91 | 20.4 | 10.0 | 64.94 | 27.33 | 3.9 | 14.20 | 5.83 | 6 | 33.83 | 16.69 | 5.95 | 38.53 | 3.88 |
| 92 | 26 | 19.5 | 66.07 | 34.45 | 8 | 18.21 | 5.6 | 6.2 | 34.7 | 19.23 | 8.2 | 35.24 | 4.79 |
| 93 | 24 | 10.0 | 72.39 | 28.04 | 2.74 | 16.24 | 5.71 | 6.4 | 36.52 | 11.04 | 2.09 | 41.26 | 4.03 |
| 94 | 20.8 | 6.0 | 71.41 | 33.36 | 1.45 | 19.06 | 5.81 | 6.5 | 33.6 | 15.91 | 5.26 | 51.61 | 3.87 |
| 95 | 22.5 | 14.0 | 70.26 | 34.67 | 8.74 | 19.49 | 5.65 | 6.3 | 34.32 | 17.34 | 6.52 | 28.47 | 5.29 |
| 96 | 16.8 | 10.0 | 60.72 | 32.51 | 2.44 | 15.79 | 5.74 | 6.2 | 30.3 | 18.44 | 6.72 | 39.54 | 4.19 |
| 97 | 21.7 | 12.0 | 69.63 | 25.51 | 4.71 | 14.21 | 6.02 | 6.4 | 37.18 | 11.94 | 3.55 | 33.84 | 4.96 |
| 98 | 18.3 | 7.0 | 67.62 | 29.01 | 3.13 | 15.69 | 5.8 | 6.1 | 39.88 | 13.54 | 4.88 | 52.31 | 6.72 |
| 99 | 21.5 | 9.0 | 67.33 | 30.13 | 1.58 | 16.23 | 5.78 | 6 | 37.13 | 14.09 | 4.91 | 34.41 | 6.51 |
| 100 | 25.9 | 24.0 | 80.19 | 38.19 | 8.7 | 24.50 | 5.66 | 6.4 | 33.64 | 18.39 | 7.35 | 44.02 | 5.29 |
| 101 | 17.8 | 7.0 | 59.1 | 26.09 | | 12.34 | 5.69 | 6.7 | 38.7 | 12.06 | 3.45 | 75.18 | 3.79 |
| 102 | 22.7 | 13.0 | 70.37 | 32.7 | 1.79 | 18.41 | 5.71 | 6.6 | 39.45 | 10.27 | 2.44 | 68.00 | 3.36 |
| 103 | 16.6 | 9.5 | 64.84 | 31.48 | 2.03 | 16.33 | 5.76 | 6.9 | 39.09 | 11.17 | 2.93 | 66.27 | 3.52 |
| 104 | 14.5 | 4.5 | 59.12 | 28.63 | 0.81 | 13.54 | 5.8 | 6.5 | 39.08 | 14.07 | 6.2 | 79.39 | 3.50 |
| 105 | 23.9 | 13.5 | 68.81 | 43.62 | 4.95 | 24.01 | 5.69 | 6.5 | 37.06 | 13.55 | 4.65 | 52.21 | 4.37 |
| 106 | 16.6 | 13.5 | 60.4 | 31.42 | 5.02 | 15.18 | 5.74 | 6.4 | 35.79 | 15.46 | 5.85 | 38.45 | 5.12 |
| 107 | 20.1 | 10.5 | 65.71 | 37.42 | 2.96 | 19.67 | 5.66 | 6.3 | 33.77 | 16.29 | 6.96 | 33.66 | 4.19 |
| 108 | 23 | 8.5 | 65.99 | 32.69 | 2.81 | 17.26 | 5.72 | 6.9 | 33.68 | 18.85 | 8.07 | 54.66 | 3.24 |
| 109 | 21.3 | 15.0 | 67.25 | 37.72 | 4.66 | 20.29 | 5.74 | 7.1 | 33.58 | 14.2 | 4.85 | 81.15 | 4.05 |
| 110 | 22.7 | 17.0 | 54.36 | 31.69 | 2.09 | 13.78 | 5.71 | 6.5 | 35.23 | 18.26 | 7.89 | 40.44 | 4.59 |
| 111 | 19.4 | 7.5 | 66.82 | 45.94 | 2.79 | 24.56 | 5.78 | 6.2 | 34.39 | 15.8 | 5.42 | 52.61 | 3.86 |
| 112 | 19.7 | 7.5 | 64.7 | 36.85 | 8.23 | 19.07 | 5.93 | 6 | 37.27 | 11.16 | 1.92 | 58.84 | 3.18 |
| 113 | 18 | 12.0 | 66.95 | 28.05 | 2.76 | 15.02 | 5.77 | 6.3 | 38.31 | 11.26 | 1.96 | 45.99 | 4.65 |
| 114 | 23.4 | 20.5 | 60.83 | 26 | 13.4 | 12.65 | 5.63 | 6.4 | 36.75 | 17.6 | 5.98 | 41.24 | 5.92 |

TABLE 3-continued

External parameters of meat quality

| ID | HCWT | GRfat | EMW | EMD | FatC | EMA | pHu loin | pHu temp | L* | a* | b* | SF | IMF |
|---|---|---|---|---|---|---|---|---|---|---|---|---|---|
| 115 | 27.1 | 13.5 | 81.36 | 32.6 | 3.04 | 21.22 | 5.65 | 6.4 | 40.79 | 12.26 | 3.65 | 40.14 | 4.02 |
| 116 | 27.9 | 11.5 | 70.5 | 34.92 | 3.36 | 19.69 | 5.56 | 6.5 | 39.01 | 13.27 | 3.42 | 38.96 | 3.66 |
| 117 | 19.3 | 4.0 | 59.75 | 28.66 | 1.61 | 13.70 | 5.75 | 6.2 | 38.43 | 11.29 | 3.04 | 72.80 | 3.17 |
| 118 | 19.3 | 10.0 | 66.71 | 30.84 | 2.91 | 16.46 | 5.71 | 6.5 | 40.3 | 11.15 | 3.21 | 62.14 | 4.33 |
| 119 | 22.9 | 6.0 | 70.37 | 30.89 | 4.04 | 17.39 | 5.7 | 6 | 37.62 | 12.83 | 3.9 | 55.83 | 3.84 |
| 120 | 23.6 | 10.5 | 75.38 | 29.61 | 2.6 | 17.86 | 5.67 | 6.5 | 31.79 | 18.7 | 7.23 | 74.92 | 3.46 |
| 121 | 19.6 | 5.5 | 62.93 | 33.07 | 2.71 | 16.65 | 5.71 | 6.5 | 30.54 | 16.71 | 5.93 | 62.02 | 3.80 |
| 122 | 20.1 | 8.5 | 68.49 | 29.7 | 3.03 | 16.27 | 5.76 | 6.5 | 37.78 | 11.02 | 2.86 | 57.12 | 3.92 |
| 123 | 19.5 | 15.5 | 59.53 | 29.44 | 5.21 | 14.02 | 5.74 | 6.3 | 34.17 | 19.35 | 8.68 | 56.60 | 5.44 |
| 124 | 20.4 | 11.5 | 68.7 | 36.82 | 2.49 | 20.24 | 5.82 | 6.1 | 39.08 | 13.65 | 5.63 | 43.75 | 5.07 |
| 125 | 18.7 | 3.5 | 69.98 | 23.27 | 2.92 | 13.03 | 5.84 | 6 | 35.61 | 12.06 | 3.65 | 67.24 | 3.67 |
| 126 | 16.4 | 7.0 | 66.08 | 28.98 | 3.13 | 15.32 | 5.73 | 6.3 | 36.01 | 12.54 | 4.63 | 79.69 | 4.42 |
| 127 | 18.9 | 10.5 | 67.51 | 28 | 8.99 | 15.12 | 5.74 | 6.1 | 34.23 | 18.98 | 9.04 | 44.18 | 5.02 |
| 128 | 24.6 | 14.5 | 61.28 | 36.31 | 7.42 | 17.80 | 5.68 | 6.3 | 35.92 | 15.67 | 5.98 | 47.51 | 4.25 |
| 129 | 23.8 | 11.5 | 66.17 | 35.95 | 3.68 | 19.03 | 5.73 | 6.2 | 34.07 | 13.76 | 4.32 | 39.30 | 4.99 |
| 130 | 22.3 | 15.5 | 74.23 | 31.05 | 12.5 | 18.44 | 5.74 | 6.5 | 31.78 | 17.87 | 7.06 | 52.81 | 4.82 |
| 131 | 20.1 | 8.0 | 70.01 | 32.34 | 1.68 | 18.11 | 5.77 | 6.3 | 33.98 | 14.5 | 4.64 | 63.94 | 3.99 |
| 132 | 18.4 | 7.5 | 60.01 | 23.86 | 2.39 | 11.45 | 5.72 | 6.3 | 34.65 | 16.4 | 7.46 | 76.05 | 4.37 |
| 133 | 17.8 | 12.5 | 66.02 | 29.46 | 2.97 | 15.56 | 5.73 | 6.2 | 35.29 | 14.34 | 5.25 | 65.67 | 5.42 |
| 134 | 18.8 | 8.0 | 64.71 | 31.63 | 1.9 | 16.37 | 5.75 | 6.2 | 37.83 | 12.3 | 4.24 | 66.29 | 4.32 |
| 135 | 19.3 | 8.0 | 67.64 | 29.8 | 3.02 | 16.13 | 5.69 | 6.4 | 40.49 | 11.87 | 3.34 | 70.76 | 3.63 |
| 136 | 21.1 | 12.0 | 65.02 | 28.44 | 4.41 | 14.79 | 5.65 | 6.2 | 32.57 | 16.73 | 6.77 | 38.56 | 4.58 |
| 137 | 16.5 | 5.0 | 59.69 | 29.36 | 1.39 | 14.02 | 5.71 | 6.5 | 39.46 | 11.57 | 3.28 | 62.13 | 5.27 |
| 138 | 21.5 | 6.5 | 64.79 | 34.47 | 2.16 | 17.87 | 5.67 | 6.2 | 38.77 | 13.24 | 4.12 | 43.64 | 5.52 |
| 139 | 20.9 | 13.0 | 62.33 | 31.55 | 5.54 | 15.73 | 5.69 | 6.2 | 39.05 | 13.68 | 4.85 | 53.34 | 5.76 |
| 140 | 18.7 | 10.5 | 62.07 | 29.45 | 5.05 | 14.62 | 5.62 | 8.1 | 35.05 | 15.72 | 6.41 | 53.69 | 4.46 |
| 141 | 19.7 | 5.5 | 73.2 | 33.71 | 2.33 | 19.74 | 5.76 | 7.9 | 39.13 | 13.87 | 4.81 | 49.80 | 4.88 |
| 142 | 18 | 5.0 | 58.85 | 30.35 | 2.28 | 14.29 | 5.57 | 7.9 | 35.69 | 15.37 | 5.87 | 53.72 | 4.57 |
| 143 | 16.9 | 5.5 | 64.31 | 29.31 | 1.18 | 15.08 | 5.56 | 8 | 36 | 13.67 | 4.15 | 44.70 | 4.29 |
| 144 | 16.3 | 6.0 | 58.13 | 21.43 | 2.01 | 9.97 | 5.66 | 8 | 35.49 | 15.36 | 5.41 | 54.34 | 4.68 |
| 145 | 20 | 9.0 | 62.92 | 25.87 | 4.71 | 13.02 | 5.71 | 8 | 38.45 | 11.88 | 2.99 | 44.78 | 4.04 |
| 146 | 17.7 | 7.5 | 67.24 | 33.43 | 3.55 | 17.98 | 5.6 | 8 | 36.82 | 11.73 | 3.27 | 38.90 | 3.66 |
| 147 | 22.7 | 5.0 | 73.9 | 21.31 | 3.52 | 12.60 | 5.89 | 8 | 33.75 | 15.74 | 5.6 | 70.86 | 3.42 |
| 148 | 19.5 | 12.5 | 63.99 | 30.1 | 4.53 | 15.41 | 5.63 | 7.9 | 34.69 | 19.85 | 8.8 | 40.19 | 6.02 |
| 149 | 18.7 | 5.5 | 68.81 | 26.24 | 2.8 | 14.44 | 5.68 | 7.7 | 39.04 | 12.9 | 4.79 | 60.02 | 3.32 |
| 150 | 20.4 | 11.0 | 65.04 | 31.18 | 3.97 | 16.22 | 5.67 | 7.6 | 32.86 | 17.86 | 7.39 | 57.13 | 3.74 |
| 151 | 18.9 | 9.0 | 66.03 | 38.9 | 3.79 | 20.55 | 5.7 | 7.9 | 33.73 | 16 | 5.5 | 39.60 | 3.83 |
| 152 | 19.3 | 6.5 | 72.01 | 29.82 | 3.31 | 17.18 | 5.97 | 8 | 40.42 | 11.62 | 3.66 | 44.35 | 4.78 |
| 153 | 18.8 | 9.0 | 66.28 | 34.4 | 2.51 | 18.24 | 5.63 | 8.1 | 38.98 | 12.55 | 3.74 | 34.52 | 4.65 |
| 154 | 21.5 | 11.0 | 66.4 | 32.38 | 2.83 | 17.20 | 5.62 | 8 | 35.26 | 16.05 | 6.32 | 53.49 | 4.32 |
| 155 | 23.2 | 17.5 | 62.46 | 32.53 | 7.75 | 16.25 | 5.66 | 8.5 | 35.8 | 15.67 | 6.22 | 42.27 | 6.00 |
| 156 | 20.2 | 13.0 | 73.23 | 30.76 | 2.23 | 18.02 | 5.65 | 8.1 | 36.61 | 15.73 | 6.02 | 43.72 | 4.82 |
| 157 | 18.7 | 14.5 | 64.92 | 32.44 | 3.29 | 16.85 | 5.71 | 8.3 | 34.62 | 14.38 | 4.71 | 69.81 | 4.20 |
| 158 | 19.6 | 6.0 | 66.2 | 36.71 | 1.93 | 19.44 | 5.6 | 8.7 | 35.13 | 15.55 | 5.43 | 79.99 | 5.31 |
| 159 | 26.1 | 26.0 | 70.09 | 42.44 | 6.65 | 23.80 | 5.64 | 8.6 | 38.71 | 14.55 | 5.73 | 48.45 | 6.04 |
| 160 | 19.8 | 6.0 | 76.13 | 36.2 | 2.8 | 22.05 | 5.69 | 8.6 | 36.21 | 15.95 | 6.09 | 59.32 | 4.50 |
| 161 | 23.1 | 9.0 | 72.96 | 33.56 | 3.48 | 19.59 | 5.79 | 8.3 | 40.33 | 12.14 | 3.61 | 56.40 | 3.76 |
| 162 | 25 | 10.0 | 69.75 | 38.08 | 4.11 | 21.25 | 5.64 | 8.3 | 42.52 | 14.04 | 5.76 | 43.13 | 6.84 |
| 163 | 17.8 | 14.5 | 52.33 | 36.67 | 1.76 | 15.35 | 5.67 | 8.3 | 37.41 | 11.79 | 2.83 | 62.60 | 4.85 |
| 164 | 21.6 | 11.5 | 65.29 | 36.95 | 3.16 | 19.30 | 5.69 | 8.6 | 34.91 | 14.33 | 5.2 | 56.61 | 3.66 |
| 165 | 22.6 | 14.0 | 62.71 | 29.48 | 4.69 | 14.79 | 5.57 | 8.1 | 34.34 | 15.91 | 6 | 61.55 | 3.95 |
| 166 | 27 | 10.0 | 79 | 33.84 | 4.24 | 21.39 | 5.6 | 8.2 | 32.06 | 15.88 | 6.15 | 70.12 | 3.88 |
| 167 | 25.1 | 13.5 | 70.08 | 35.07 | 5.5 | 19.66 | 5.85 | 8.3 | 37.83 | 12.28 | 4.07 | 75.32 | 3.41 |
| 168 | 19.9 | 5.0 | 66.94 | 29.5 | 2.49 | 15.80 | 5.78 | 8.5 | 36.84 | 13.26 | 4.08 | 79.51 | 2.21 |
| 169 | 17.9 | 6.5 | 64.46 | 30.7 | 3.06 | 15.83 | 5.78 | 8.5 | 41.42 | 12.37 | 5.31 | 67.19 | 3.26 |
| 170 | 19.6 | 4.0 | 63.42 | 32.34 | 2.3 | 16.41 | 5.68 | 7.8 | 37.92 | 16.67 | 6.27 | 35.15 | 4.02 |
| 171 | 22.1 | 12.0 | 69.08 | 30.14 | 2.89 | 16.66 | 5.5 | 8 | 38.89 | 14.51 | 5.01 | 54.25 | 5.90 |
| 172 | 19.6 | 12.0 | 64.51 | 31.06 | 6.02 | 16.03 | 5.69 | 8.3 | 36.07 | 15.46 | 5.18 | 93.15 | 3.00 |
| 173 | 19.9 | 3.5 | 70.97 | 28.59 | 3.79 | 16.23 | 5.65 | 8.1 | 34.99 | 13.79 | 4.33 | 52.49 | 3.62 |
| 174 | 22.1 | 14.0 | 64.05 | 41.44 | 4.54 | 21.23 | 5.62 | 8.4 | 36.16 | 15.09 | 5.06 | 31.72 | 4.60 |
| 175 | 18.3 | 8.0 | 61.55 | 22.86 | 3.98 | 11.26 | 5.86 | 8 | 29.3 | 16.24 | 5.5 | 40.79 | 3.29 |
| 176 | 24.6 | 13.5 | 67.79 | 36.9 | 2.77 | 20.01 | 5.52 | 8 | 38.46 | 15.76 | 5.85 | 58.54 | 3.53 |
| 177 | 22.2 | 9.0 | 67.35 | 24.9 | 3.13 | 13.42 | 5.7 | 8.1 | 32.88 | 15.31 | 5.17 | 50.41 | 3.99 |
| 178 | 26.6 | 13.5 | 76.31 | 40.94 | 4.94 | 24.99 | 5.92 | 8 | 32.28 | 18.62 | 6.64 | 38.51 | 4.45 |
| 179 | 20.1 | 7.0 | 72.84 | 30.88 | 6.11 | 17.99 | 5.57 | 8.4 | 38.86 | 12.05 | 3.42 | 38.88 | 3.81 |
| 180 | 23.7 | 13.0 | 65.16 | 30.13 | 4.4 | 15.71 | 5.74 | 8.5 | 38.77 | 19.16 | 9.48 | 39.48 | 4.83 |
| 181 | 22.4 | 11.5 | 66.94 | 30.23 | 3.34 | 16.19 | 5.59 | 8 | 36.27 | 15.04 | 5.83 | 45.15 | 4.14 |
| 182 | 18 | 10.5 | 68.57 | 25.71 | 3.08 | 14.10 | 5.58 | 8.5 | 34.82 | 13.78 | 4.07 | 42.49 | 3.80 |
| 183 | 20.7 | 3.5 | 75.61 | 32.65 | 0.21 | 19.75 | 5.71 | 8.1 | 33.78 | 16.02 | 5.86 | 82.34 | 2.92 |
| 184 | 19.2 | 6.5 | 66.31 | 25.23 | 2.84 | 13.38 | 5.93 | 8.4 | 35.91 | 12.89 | 4.34 | 61.12 | 2.63 |
| 185 | 20.8 | 5.0 | 65.6 | 24.42 | 1.88 | 12.82 | 5.74 | 8 | 33.26 | 16.83 | 6.41 | 60.26 | 3.11 |
| 186 | 23.4 | 15.5 | 73 | 32.68 | 5.31 | 19.09 | 5.6 | 7.9 | 35.07 | 15.78 | 6.26 | 51.41 | 4.31 |
| 187 | 25.1 | 22.0 | 76.99 | 33.84 | 7.07 | 20.84 | 5.61 | 8.4 | 34.72 | 17.82 | 7.18 | 45.13 | 4.61 |
| 188 | 23.6 | 20.5 | 66.42 | 30.48 | 9.96 | 16.20 | 5.65 | 8.5 | 37.69 | 14.03 | 5.16 | 45.73 | 4.97 |
| 189 | 21.7 | 10.5 | 71.48 | 32.75 | 2.17 | 18.73 | 5.84 | 8 | 31.4 | 15.15 | 5.34 | 49.12 | 3.79 |

TABLE 3-continued

External parameters of meat quality

| ID | HCWT | GRfat | EMW | EMD | FatC | EMA | pHu loin | pHu temp | L* | a* | b* | SF | IMF |
|---|---|---|---|---|---|---|---|---|---|---|---|---|---|
| 190 | 23.2 | 17.5 | 76.43 | 24.78 | 4.95 | 15.15 | 5.79 | 8 | 38.87 | 15.03 | 5.44 | 57.23 | 5.15 |
| 191 | 21.1 | 9.0 | 75.81 | 30.05 | 4.27 | 18.22 | 5.64 | 7.6 | 39.23 | 14.71 | 6.26 | 49.34 | 4.96 |
| 192 | 20.8 | 6.0 | 71.9 | 30.72 | 2.88 | 17.67 | 6 | 8 | 36.31 | 11.64 | 2.82 | 71.46 | 3.19 |
| 193 | 23.9 | 15.5 | 69.72 | 25.85 | 4.56 | 14.42 | 5.54 | 8 | 32.98 | 15.79 | 5.71 | 53.32 | 6.36 |
| 194 | 27.7 | 14.5 | 67.04 | 38.37 | 3.42 | 20.58 | | | 38.71 | 16.18 | 6.72 | 48.65 | 5.10 |
| 195 | 21.8 | 18.5 | 73.1 | 34.76 | 3.73 | 20.33 | 5.75 | 7.8 | 38.26 | 13.71 | 4.59 | 47.60 | 4.37 |
| 196 | 18.3 | 11.5 | 78.12 | 31.56 | 4.5 | 19.72 | 5.67 | 8.3 | 33.23 | 15.1 | 5.2 | 56.35 | 2.98 |
| 197 | 21.3 | 8.0 | 60.76 | 20.3 | 3.36 | 9.87 | 5.56 | 8.3 | 34.67 | 20.99 | 9.55 | 50.18 | 3.41 |
| 198 | 19.1 | 4.5 | 70.56 | 22.21 | 2.9 | 12.54 | 5.9 | 8.3 | 35.24 | 18.77 | 7.91 | 52.51 | 3.48 |
| 199 | 24.2 | 16.5 | 70.01 | 33.36 | 6.61 | 18.68 | 5.67 | 8.4 | 35.1 | 15.3 | 5.93 | 57.6 | 4.48 |
| 200 | 23.7 | 12.0 | 68.58 | 32.42 | 4.45 | 17.79 | 5.64 | 8.5 | 38.95 | 11.54 | 2.81 | 56.58 | 3.13 |

APPENDIX B—COMPARISON OF STATISTICS FOR EACH DATA SET

Figure 10:
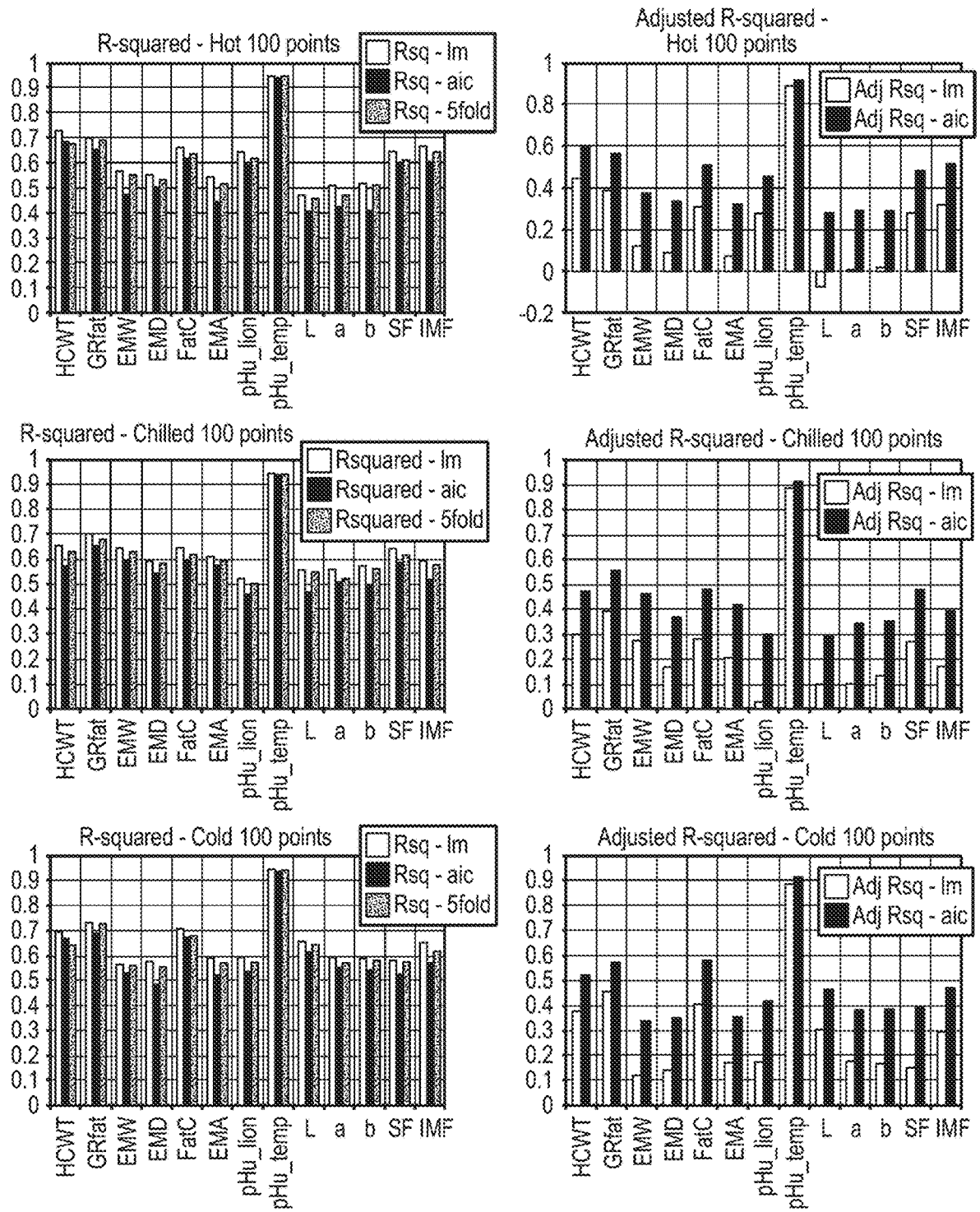
FIG. 10 shows R-squared and Adjusted R-squared values for all data sets. lm—linear model, aic—Akaike's Information Criterion, 5fold—k-fold Cross Validation method with 5 folds.

FIG. 10 shows R-squared and Adjusted R-squared values for all data sets. lm—linear model, aic—Akaike's Information Criterion, 5 fold-k-fold Cross Validation method with 5 folds.

Figure 11:
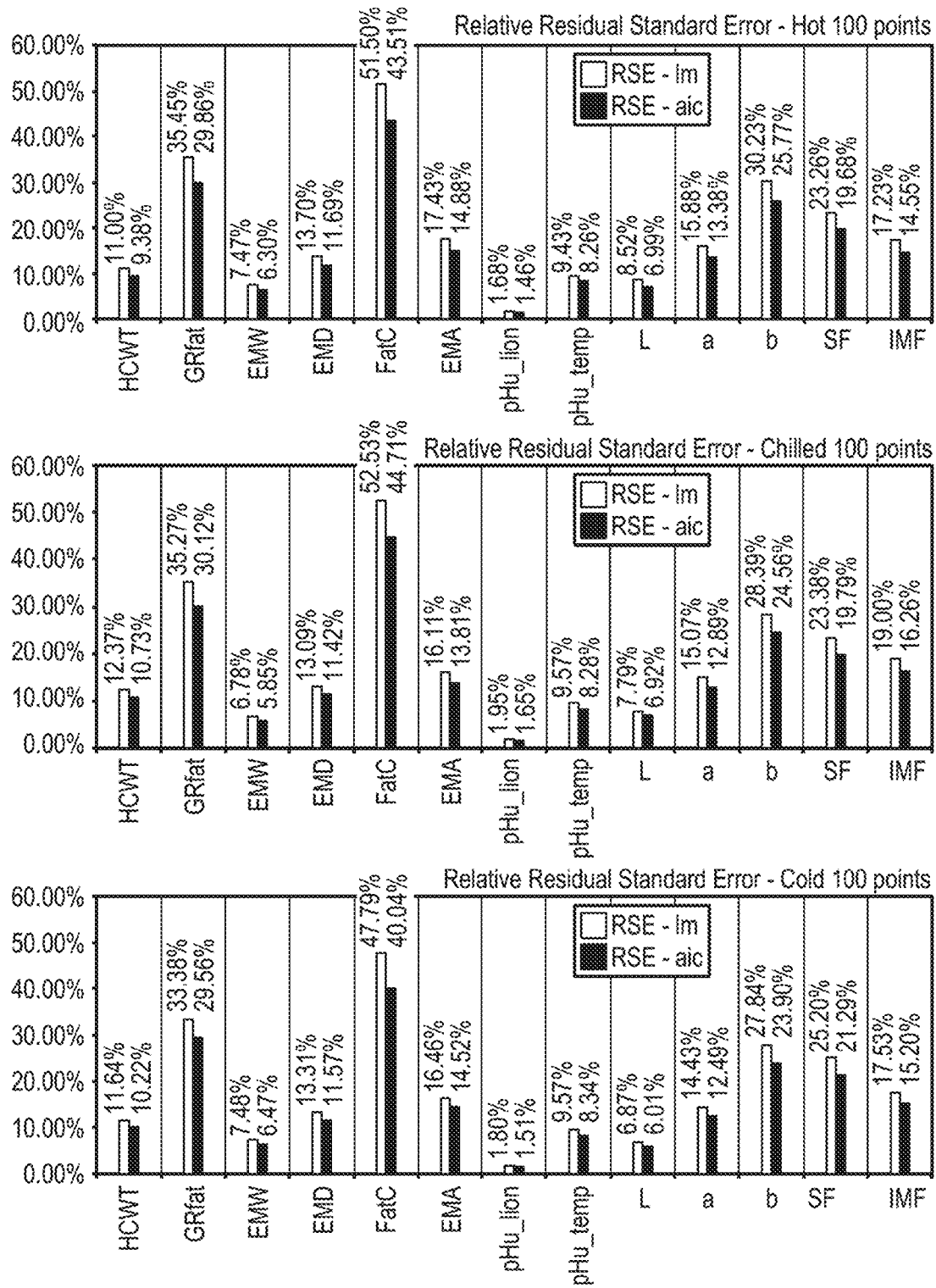
FIG. 11 shows relative Residual Standard Error (RSE) and F-Statistics values for all data sets. lm—linear model, aic—Akaike's Information Criterion.
Figure 11:
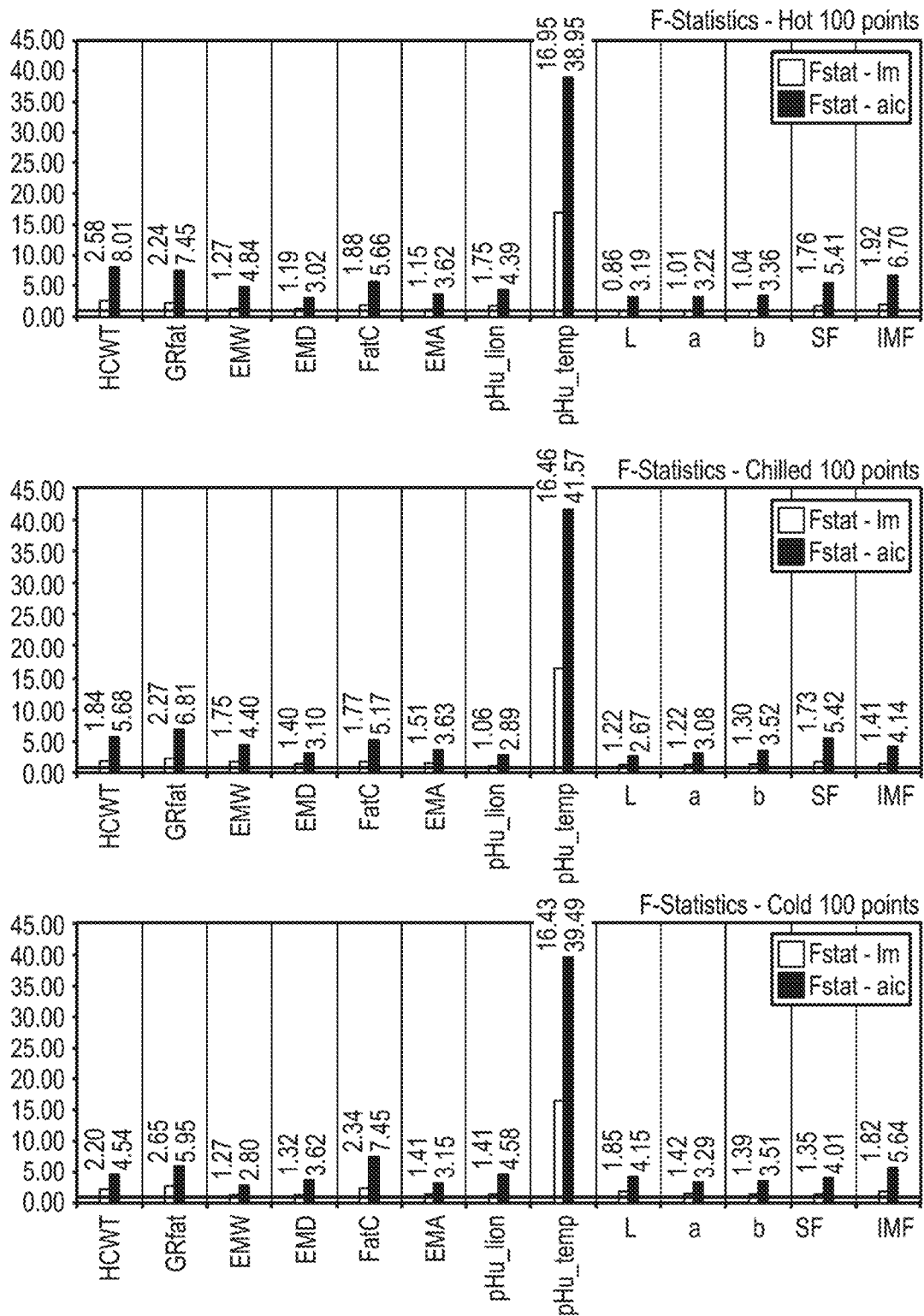

FIG. 11 shows relative Residual Standard Error (RSE) and F-Statistics values for all data sets. lm—linear model, aic—Akaike's Information Criterion. F-Statistic value is considered good if it is much larger than 1 (shown as black lines).

Figure 12:
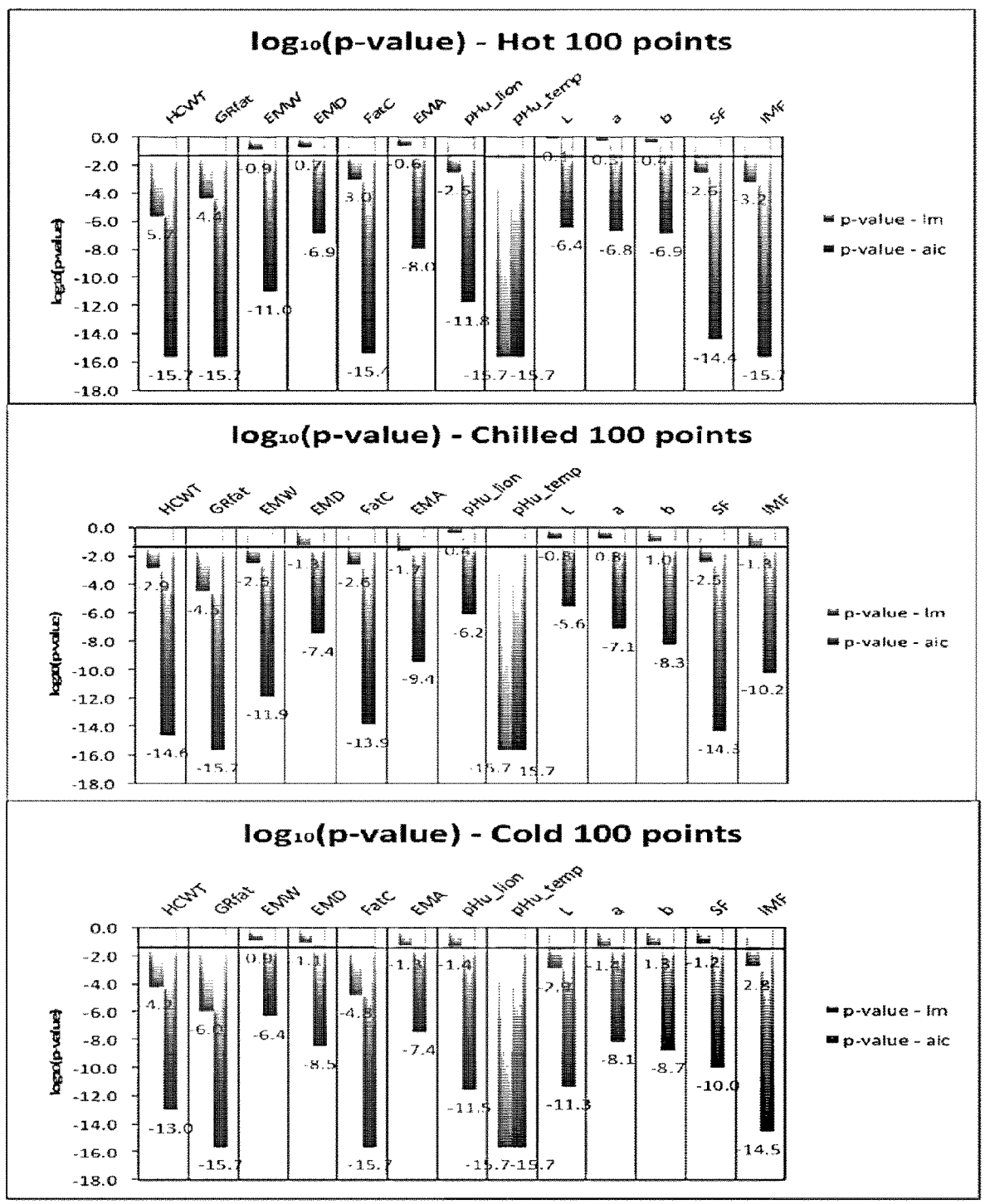
FIG. 12 shows log 10(p-value) for all data sets. lm—linear model, aic—Akaike's Information Criterion.

FIG. 12 shows $\log_{10}$(p-value) for all data sets. lm—linear model, aic—Akaike's Information Criterion. Black line shows the position of threshold $\log_{10}(0.05) \approx -1.3$, where values below it allow to reject the null-hypothesis.

EXAMPLE 3

Measurement and Analysis of IMF, Shear Force and pH of Beef Carcasses (Hot and Cold)

Figure 13:
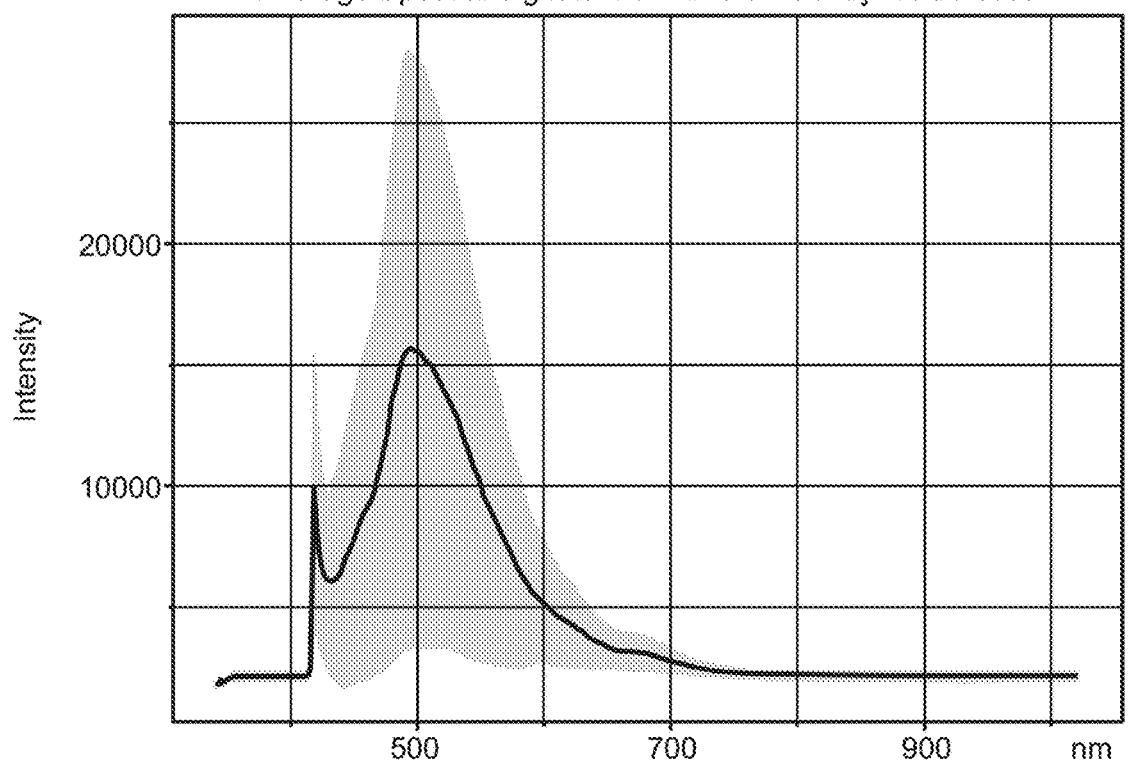
FIG. 13 shows the average spectral signature for the hot carcass according to another embodiment.

Measurements were performed across two days. On the first day, 159 hot beef carcasses were scanned using the first version of the optical apparatus 38 as described above with the probe needle 16 attached directly to the bifurcated fibre 18. 139 body analyses were obtained with 20 bodies excluded due to either poor scan or missing variables. The integration time was approximately 80 ms and spectral signatures were not normalised. The average spectral signature from the hot beef plus a variance is shown in FIG. 13. Any spectral signature with an intensity of <5000 at 500 nm was excluded as this was likely due to an accidental scan outside of the meat.

Figure 14:
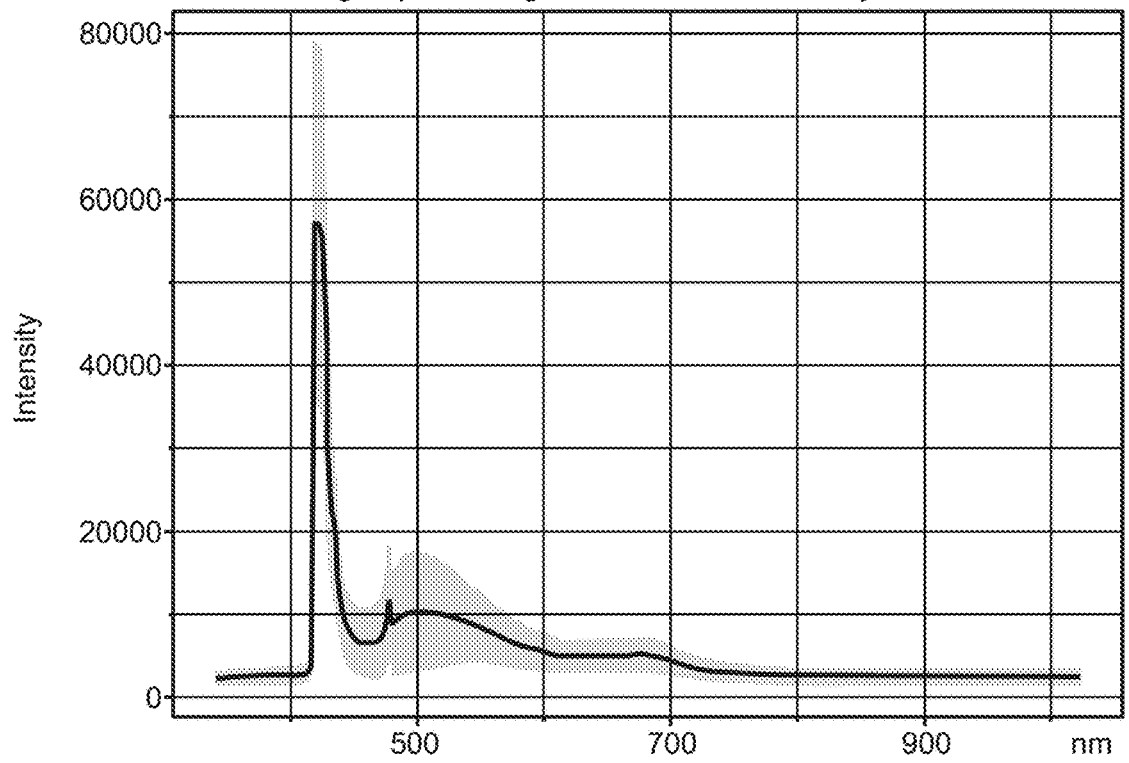
FIG. 14 shows the average spectral signature of the cold carcass according to another embodiment.

On the second day, the same 159 carcasses, now cold, were scanned using the same apparatus except that the probe needle 16 was attached to the bifurcated fibre 18 via a patch cable. 124 body analyses were obtained with 35 bodies excluded due to either poor scan or missing variable data. The integration time was approximately 100 ms. The average spectral signature from the cold beef plus a variance is shown in FIG. 14. Any spectral signature with an intensity of <1000 at 500 nm was excluded as this was likely due to an accidental scan outside of the meat. Despite an integration time of approximately 100-150 ms, the signal from meat the meat was extremely low. This made background subtraction problematic. Also, the use of a patch cable reduced the collection efficiency compared to the measurements made on the first day.

After processing of the data and linear model generation with Akaike's Information Criterion, it was found that IMF, SF, and pH have an approximate R2 value of 0.4-0.5 in hot carcasses (FIGS. 14-16) and IMF, SF, and pH have an approximate R2 value of 0.5-0.6 in cold carcasses (FIGS. 17-20).

Figure 15:
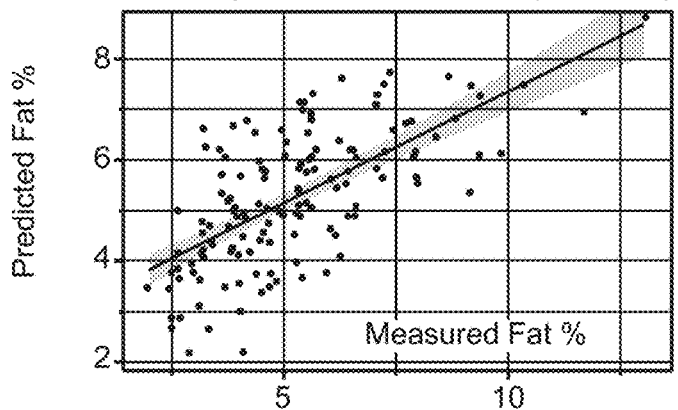
FIG. 15 shows measured percentage of intra-muscular fat vs predicted percentage of intra-muscular fat for the hot carcass.

FIG. 15 shows measured percentage of intra-muscular fat vs predicted percentage of intra-muscular fat for the hot carcass. The prediction of intra-muscular fat percentage has an R2 of 0.44 using a Linear model with AIC.

Figure 16:
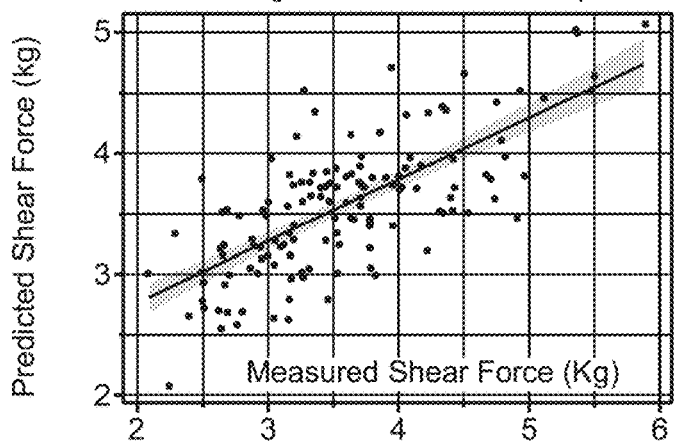
FIG. 16 shows measured shear force vs predicted shear force for the hot carcass.

FIG. 16 shows measured shear force vs predicted shear force for the hot carcass. The prediction of shear force has an R2 of 0.51 using Linear model with AIC.

Figure 17:
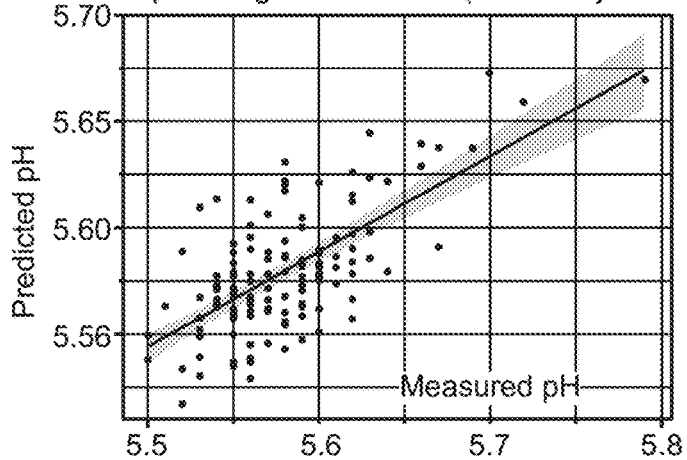
FIG. 17 shows measured pH vs predicted pH for the hot carcass.

FIG. 17 shows measured pH vs predicted pH for the hot carcass. The prediction of pH has an R2 of 0.45 using Linear model with AIC.

Figure 18:
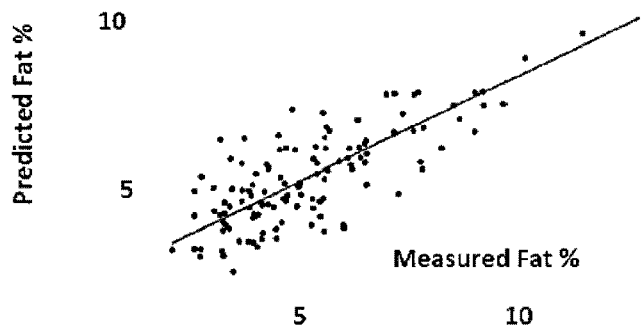
FIG. 18 shows measured percentage of intra-muscular fat vs predicted percentage of intra-muscular fat for the cold carcass.

FIG. 18 shows measured percentage of intra-muscular fat vs predicted percentage of intra-muscular fat for the cold carcass. The prediction of intra-muscular fat percentage has an R2 of 0.63 using a Linear model with AIC.

Figure 19:
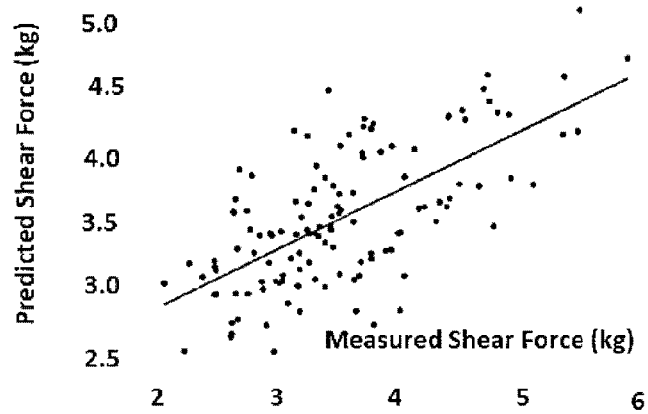
FIG. 19 shows measured shear force vs predicted shear force for the cold carcass.

FIG. 19 shows measured shear force vs predicted shear force for the cold carcass. The prediction of shear force has an R2 of 0.66 using Linear model with AIC.

Figure 20:
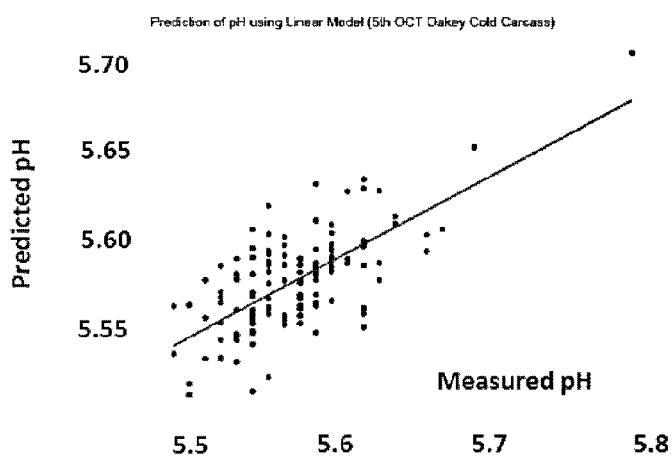
FIG. 20 shows measured pH vs predicted pH for the cold carcass.

FIG. 20 shows measured pH vs predicted pH for the cold carcass. The prediction of pH has an R2 of 0.48 using Linear model with AIC.

Although the present disclosure has been described with reference to particular examples, it will be appreciated by those skilled in the art that the disclosure may be embodied in many other forms.

It is to be understood that various alterations, additions and/or modifications may be made to the parts previously described without departing from the ambit of the present disclosure, and that, in the light of the above teachings, the present disclosure may be implemented in software, firmware and/or hardware in a variety of manners as would be understood by the skilled person.

As used herein, the singular forms "a," "an," and "the" may refer to plural articles unless specifically stated otherwise.

Throughout this specification, unless the context requires otherwise, the word "comprise", or variations such as "comprises" or "comprising", will be understood to imply the inclusion of a stated element or integer or group of elements or integers but not the exclusion of any other element or integer or group of elements or integers.

All methods described herein can be performed in any suitable order unless indicated otherwise herein or clearly contradicted by context. The use of any and all examples, or exemplary language (e.g., "such as") provided herein, is intended merely to better illuminate the example embodiments and does not pose a limitation on the scope of the claimed invention unless otherwise claimed. No language in the specification should be construed as indicating any non-claimed element as essential.

The description provided herein is in relation to several embodiments which may share common characteristics and features. It is to be understood that one or more features of one embodiment may be combinable with one or more features of the other embodiments. In addition, a single feature or combination of features of the embodiments may constitute additional embodiments.

The subject headings used herein are included only for the ease of reference of the reader and should not be used to limit the subject matter found throughout the disclosure or the claims. The subject headings should not be used in construing the scope of the claims or the claim limitations.

Future patent applications may be filed on the basis of the present application, for example by claiming priority from the present application, by claiming a divisional status and/or by claiming a continuation status. It is to be understood that the following claims are provided by way of example only, and are not intended to limit the scope of what may be claimed in any such future application. Nor should the claims be considered to limit the understanding of (or exclude other understandings of) the present disclosure. Features may be added to or omitted from the example claims at a later date.

The invention claimed is:

1. A method of assessing quality of a meat product, the method comprising:
   receiving data representative of autofluorescent light emitted from the meat product upon application of incident laser light from a probe inserted into the meat product;
   analysing the data to determine one or more parameters indicative of quality of the meat product; and
   assessing the quality of the meat product on the basis of the one or more parameters.

2. The method according to claim 1, wherein the received data comprises spectral data excited by the application of laser light to the meat product.

3. The method according to claim 2, wherein the spectral data comprises data in the range of 350 nm to 1100 nm.

4. The method according to claim 1, wherein the one or more parameters comprise one or more of:
   a parameter indicative of intra-muscular fat (IMF parameter);
   a parameter indicative of shear force (SF parameter);
   a parameter indicative of pH of the meat product; and
   a parameter indicative of colour of the meat product.

5. The method according to claim 4, wherein the data is analysed using one or more models to predict the one or more parameters.

6. The method according to claim 5, wherein the one or more models are created using training data comprising data representative of light emitted from a plurality of sample meat products upon application of incident light to the sample meat products, wherein each sample meat product has pre-determined values for the one or more parameters.

7. The method according to claim 1, wherein the data comprises spectral data which is processed prior to analysis to reduce a number of data points across the spectral range.

8. The method according to claim 1, wherein the meat product is a carcass, a part of a carcass, a cut of meat from the carcass, or a processed product derived from the carcass or the cut of meat.

9. A meat product graded according to a method of claim 1.

10. A computer-readable memory medium comprising instructions that, when executed by a processor, cause the processor to carry out the method of claim 1.

11. A system for assessing quality of a meat product, the system comprising:
    a light source for applying incident laser light from a probe inserted into the meat product;
    a measuring device for producing data representative of autofluorescent light emitted from the meat product upon application of the incident laser light to the meat product;
    a processor;
    a computer-readable memory medium comprising instructions that, when executed by the processor, cause the processor to carry out the method of claim 1.

12. The system according to claim 11, wherein the processor is in physical data connection with the measuring device or in data connection locally with the measuring device.

13. The system according to claim 11, wherein the light source and the measuring device comprise part of the probe, and the processor and the computer-readable memory medium are located remotely from the probe and receive the data over the internet.

14. A system for assessing quality of a meat product, the system comprising:
    a light source for applying incident laser light from a probe inserted into the meat product;
    a measuring device for producing data representative of autofluorescent light emitted from the meat product upon application of the incident laser light to the meat product;
    a processor;
    a computer-readable memory medium comprising instructions that, when executed by the processor, cause the processor to:
      analyse the data to determine one or more parameters indicative of quality of the meat product, and
      provide a measure of the quality of the meat product on the basis of the one or more parameters.

15. The system according to claim 14, wherein the processor is in physical data connection with the measuring device or in data connection locally with the measuring device.

16. The system according to claim 14, wherein the light source and the measuring device comprise part of the probe, and the processor and the computer-readable memory medium are located remotely from the probe and receive the data over the internet.

17. The system according to claim 14, wherein the computer-readable medium comprises a series of instructions executable by the processor, that cause the processor to:
    receive data representative of light emitted from the meat product upon application of the incident laser light to the meat product;
    analyse the data to determine one or more parameters indicative of quality of the meat product;
    provide a measure of the quality of the meat product on the basis of the one or more parameters; and
    assess the quality of the meat product on the basis of the one or more parameters.

18. A method of creating one or more models for assessing quality of a meat product, the method comprising:
    for a plurality of sample meat products, receiving data representative of autofluorescent light emitted from the sample meat product upon application of incident laser light from a probe inserted into the sample meat product;

for the sample meat products, receiving one or more pre-determined values;

using the data and one or more pre-determined values to create one or more models to predict one or more parameters indicative of quality of the meat product.

\* \* \* \* \*